United States Patent [19]

Cronin et al.

[11] 4,007,184

[45] Feb. 8, 1977

[54] SUBSTITUTED ALKYL ESTERS OF QUINOXALINE-DI-N-OXIDE-2-CARBOXYLIC ACID

[75] Inventors: Timothy H. Cronin, East Lyme; Kenneth Richardson, Groton, both of Conn.

[73] Assignee: Pfizer Inc., New York, N.Y.

[22] Filed: Oct. 9, 1975

[21] Appl. No.: 621,219

Related U.S. Application Data

[60] Division of Ser. No. 397,162, Sept. 13, 1973, Pat. No. 3,915,975, which is a division of Ser. No. 135,792, April 20, 1971, Pat. No. 3,818,007, and a continuation-in-part of Ser. No. 20,841, March 18, 1970, abandoned.

[52] U.S. Cl. ............................................. 260/250 QN
[51] Int. Cl.$^2$ ........................................ C07D 241/52
[58] Field of Search ............... 260/250 Q, 250 QN

[56] References Cited

UNITED STATES PATENTS 3,907,994   9/1975   Cronin et al. ............... 260/250 QN

*Primary Examiner*—Alton D. Rollins
*Assistant Examiner*—Mark L. Berch
*Attorney, Agent, or Firm*—Connolly and Hutz

[57] ABSTRACT

Novel alkyl esters of quinoxaline-di-N-oxide-2-carboxylic acid substituted on the alkyl portion of the ester by hydroxy, acyloxy, N-alkyl carbamyloxy, dialkylaminoacyloxy, carboxyacyloxy, alkoxycarbonyloxy, haloacyloxy, amino and mono- and disubstituted amino, useful as antibacterial agents and in promoting growth and improving feed efficiency of animals in general.

1 Claim, No Drawings

SUBSTITUTED ALKYL ESTERS OF QUINOXALINE-DI-N-OXIDE-2-CARBOXYLIC ACID

CROSS REFERENCE TO RELATED APPLICATIONS

This application is a division of application Ser. No. 397,162, filed Sept. 13, 1973, now U.S. Pat. No. 3,915,975 which in turn is a division of application Ser. No. 135,792, filed Apr. 20, 1971 and now U.S. Pat. No. 3,818,007, which in turn is a continuation-in-part of application Ser. No. 20,841, filed Mar. 18, 1970 and now abandoned.

BACKGROUND OF THE INVENTION

This invention relates to quinoxaline-di-N-oxides, and more particularly to a unique series of 3-methyl-quinoxaline-di-N-oxide-2-carboxylic acid alkyl esters, substituted on the alkyl portion of the ester by hydroxy, acyloxy, N-alkyl carbamyloxy, dialkylaminoacyloxy, carboxyacyloxy, alkoxycarbonyloxy, haloacyloxy, amino and mono- and disubstituted amino and the appropriate basic, quaternary and acid addition salts thereof possessing antibacterial activity against pathogenic microorganisms and to methods for the promotion of weight gain and food consumption of animals.

Continuing efforts to uncover new and more useful antibacterial agents have led, over the years, to the development of a wide variety of prototype organic compounds including numerous congeners of quinoxaline-di-N-oxides. Landquist, et al., J. Chem. Soc., 2052 (1956), in a search for compounds of improved antibacterial or antiprotozoal activity, reported the preparation of several derivatives of 2-methyl- and 2,3-dimethylquinoxaline-di-N-oxides in which the methyl groups were converted to groups such as bromomethyl-, acetoxymethyl- and hydroxymethyl including 3-methyl-2-carbethoxyquinoxaline-di-N-oxide. However, no utility is alleged for any of these compounds. French Pat. No. M3717, granted Jan. 3, 1966, discloses 2-quinoxaline-carboxamide-di-N-oxides in which the carboxamide group may be substituted with an alkyl, substituted alkyl, aryl, aralkyl, or cycloalkyl group. Also disclosed, but the structure not indicated, are the corresponding 2-quinoxaline-carboxylic acid substituted esters. They are reported to be of use in human therapy as antitubercular, antibacterial, anticancer, antivirus and antiprotozoal agents.

Belgian Pat. No. 697,976, granted Nov. 3, 1967, describes a variety of N-substituted derivatives of 3-methyl-2-quinoxalinecarboxamide-di-N-oxide in which the N-substituent is phenyl, substituted phenyl, dodecyl or ethyl, as well as the corresponding 3-methyl-2-carbethoxyquinoxaline-di-N-oxide. They are said to be of value as intermediates for the preparation of vegetation protection agents and pharmaceutical agents. Belgian Pat. Nos. 721,724; 721,725; 721,726; 721,727 and 721,728; published Apr. 2, 1969, describe a variety of N-substituted 3-methyl-2-quinoxalinecarboxamide-di-N-oxide derivatives wherein the N-substituent is a hydroxyalkyl, lower alkoxyalkyl, carboalkoxyalkyl, monoalkylaminoalkyl or di(alkyl)aminoalkyl group as antibacterial agents.

SUMMARY OF THE INVENTION

The novel antibacterial and growth promotant quinoxaline-di-N-oxides of this invention are represented by the formula:

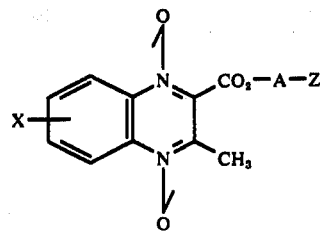

wherein
X is a substituent at the 6- or 7-position selected from the group consisting of hydrogen, fluorine, chlorine, bromine, trifluoromethyl, methyl and methoxy;

A is alkylene of from 2 to 5 carbon atoms; and

Z is selected from the group consisting of: (1) hydroxy; (2) acyloxy of the formula —O$_2$CR wherein R is selected from the group consisting of hydrogen; alkyl containing from 1 to 10 carbon atoms; alkoxy containing from 1 to 4 carbon atoms; alkylamino containing from 1 to 4 carbon atoms; carboxyalkyl containing from 2 to 8 carbon atoms; and substituted alkyl wherein said alkyl contains from 1 to 3 carbon atoms and said substituent is selected from the group consisting of chlorine, bromine and dialkylamino wherein said alkyl contains from 1 to 3 carbon atoms; (3) amino; (4) monosubstituted amino of the formula NHR$_1$ wherein R$_1$ is alkyl containing from 1 to 4 carbon atoms; (5) disubstituted amino of the formula NR$_2$R$_3$ wherein R$_2$ and R$_3$ are each alkyl containing from 1 to 2 carbon atoms;

acid addition salts thereof wherein Z is selected from the group consisting of amino, monosubstituted amino, disubstituted amino, and dialkylaminoacyloxy; pharmaceutically acceptable basic salts thereof wherein Z is carboxyacyloxy; and lower alkyl pharmaceutically acceptable quaternary salts thereof wherein Z is dialkylaminoacyloxy.

Of particular interest, because of their in vitro and in vivo anti-bacterial activity and animal growth promotant activity, are compounds wherein X is hydrogen or chlorine, A is alkylene of from 2 to 3 carbon atoms and Z is hydroxy, acetoxy, n-octanoyloxy, (ethoxycarbonyl)oxy, 3-carboxypropionyloxy, 4-carboxybutyryloxy, amino, dimethylamino or methylethylamino.

Also considered within the scope of this invention are congeners of the aforementioned compounds where the 3-methyl substituent is replaced by lower alkyl containing from 2 to 3 carbon atoms; where Z is acyloxy of the formula —O$_2$CR, wherein R is phenyl and substituted phenyl, the substituent being selected from the group consisting of halo (F, Cl, Br), lower alkoxy, lower alkyl and lower dialkylamino; where A is part of a cycloalkyl group containing from 3 to 8 carbon atoms and where A, as alkylene or part of a cycloalkyl group is substituted by hydroxy. Also included within the purview of the present application are those congeners wherein the acyl portion of the carboxyacyloxy group, Z, is derived from a cycloalkylcarboxylic acid or an aromatic acid, including benzoic acids, napthalenecarboxylic acids and heterocyclic acids.

Also contemplated is polycarboxyacyloxy as being represented by the variable Z. In like manner these compounds also possess antibacterial and growth promotant activity.

DETAILED DESCRIPTION OF THE INVENTION

In accordance with the process employed for preparing 3-methyl-2-quinoxalinecarboxylic acid alkyl esters of the instant invention, an appropriately substituted benzofuroxan is contacted with an acetoacetic ester derivative as illustrated in the following scheme:

skilled in the art. For instance, the synthesis of variously substituted benzofuroxans is described by Kaufman, et al., in *Advan. Heterocyclic Chem.*, 10, 1 (1969). Acetoacetates are readily prepared from diketene according to the general procedure of Brintzinger, et al., *Chem. Ber.*, 83, 103 (1950).

Quinoxaline-di-N-oxides of the instant invention result from the condensation of benzofuroxan and substituted benzofuroxans with acetoacetic esters such that the 2- and 3-positions of the resulting annellated structure represent the carbonyl carbon and the carbon of

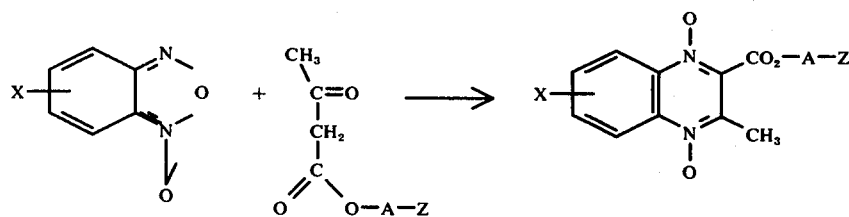

wherein X and A are as previously defined, and Z is alkanoyloxy or di-substituted amino.

As a necessary element of the herein described process, the reaction sequences described above must be effected in the presence of a base. Such a base is of varied character. For instance, it is meant to contemplate such bases as organic amines, ammonia, alkali metal hydroxides, hydrides and alkoxides. Representative of such bases are ammonia, primary amines such as n-propylamine, n-butylamine, aniline, cyclohexylamine, benzylamine, -toluidine, ethylamine, octylamine, tertiary amines such as diethylaniline, N-methylpyrrolidine, N,N-dimethylpyrimidine N-methylmorpholine, and 1,5-diazabicyclo-[4,3,0]-5-nonene; sodium hydroxide, potassium hydroxide, ammonium hydroxide, sodium ethoxide, potassium methoxide, and sodium hydride. The preferred base to use is an organic amine, ammonia or alkoxide.

In practice, a solution or suspension of the appropriately substituted benzofuroxan and the requisite acetoacetate in a reaction-inert solvent such as ethanol, N,N-dimethylformamide, benzene, tetrahydrofuran, chloroform or hexamethylphosphoramide is treated with an alkoxide, e.g., sodium ethoxide. It is preferable to use at least an equimolar amount of the benzofuroxan and acetoacetate, while the amount of base may be from a catalytic to equimolar amount. The reaction is carried out at ambient temperatures, although it may be heated to 100° C. to hasten product formation. Reaction time is not critical, but will vary depending on the reactivity of the starting materials, temperature and solvent employed. Substantial yields of the desired products are isolated with reaction periods of 15 minutes to 24 hours.

The requisite benzofuroxans and acetoacetates are either readily available or easily prepared by those the active methylene group of the acetoacetate.

The substituents on the benzene moiety of the 3-methyl-2-quinoxaline-carboxylic acid ester-1,4-dioxides can vary widely. For example, at least one of the following substituents can be present: hydrogen, methyl, methoxy, chloro, fluoro, bromo and trifluoromethyl. In like manner, the substituents may include methylthio, methylsulfonyl, methylsulfinyl, trifluoromethylthio, trifluoromethoxy, acetyl, amino, nitro, dimethylamino, acetamido, sulfamyl and nomo- and dimethylsulfamyl, methylsulfonylamino, mercapto, hydroxy, acetoxy, carboxy, carboxamido and mono- and dimethylcarboxamido, cyano, aldehydo and phosphono. The favored positions on the fused benzene ring of said final products are the 6- or 7-positions. The favored positions for substituents on the aryl ring of the starting benzofuroxans leading to said final products are the 5- or 6-positions. When one of said substituted benzofuroxans is condensed with the requisite acetoacetate, a 6- and 7-substituted quinoxaline-di-N-oxide are produced. This multiple product formation results because of the two orientation possibilities of the acetoacetate fragment in the final product. For example, if one reacts a 5-substituted benzofuroxan of the formula:

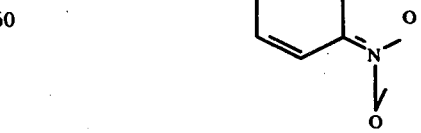

with a reactant CH$_3$COCH$_2$CO$_2$—A—Z, two products, a 6- and 7-substituted quinoxaline-di-N-oxide, result as shown by the formulae:

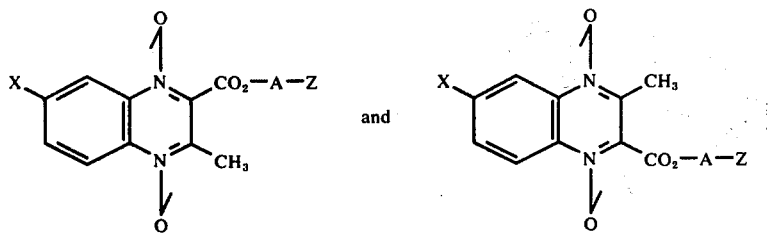
and

If the corresponding 6-substituted benzofuroxan is employed as the starting material, the same two possible products are formed.

The mixture of isomers is recovered by methods known to those skilled in the art. In many of the preparations disclosed wherein a solid, often crystalline material, separates from the reaction mixture, the solid appears to consist predominantly of one of the isomers. Said isomer can be purified by repeated recrystallization from a suitable solvent to a constant melting point. The other isomer, the one present in smaller amounts in the originally isolated solid material, is the predominant product in the mother liquor. It can be recovered therefrom by methods known to those skilled in the art, as for example, the evaporation of the mother liquor and repeated crystallization of the residue to a product of constant melting point. Alternatively, the reaction mixture can be extracted either before or after evaporation to dryness.

Although said mixtures may be separated by methods known to those skilled in the art, for practical reasons it is advantageous to use said mixtures as they are isolated from the reaction. Further, it is frequently advantageous to purify these mixtures of isomers by at least one recrystallization from an appropriate solvent or by trituration in an appropriate solvent. Said recrystallization or trituration thus allows the separation of the mixture of positional isomers from such extraneous materials as starting material and undesirable by-products.

The identification of the isomers has not been completed. Both isomers of a given compound, however, exhibit the same type of activity, e.g., as animal growth promotants or as antibacterial agents.

Compounds of the present invention wherein Z is hydroxy are most conveniently prepared from the requisite acyloxy analogs by acid hydrolysis. In practice, 3-methyl-2-quinoxalinecarboxylic acid alkyl ester, 1,4-dioxide substituted in the alkyl portion of the ester by an alkanoyloxy moiety is added to an aqueous acid solution, for instance, sulfuric, phosphoric, or hydrochloric. In general, the concentration of the acid is from about 1–12N, with a preferred range of 10–12N. The hydrolysis is effected at temperatures of from 0°–50° C. with a preferred temperature of 25°–35° C. and a reaction period of 30 minutes to 3 hours. After the reaction is completed water is added to the mixture and the pH is adjusted to pH 5 using an aqueous solution of a suitable base, e.g., sodium hydroxide. The mixture is then extracted several times with a suitable solvent such as chloroform, and the organic layer separated, dried over sodium sulfate and concentrated in vacuo to dryness.

Compounds of the present invention wherein Z is amino, $-NH_2$, are synthesized by the following scheme:

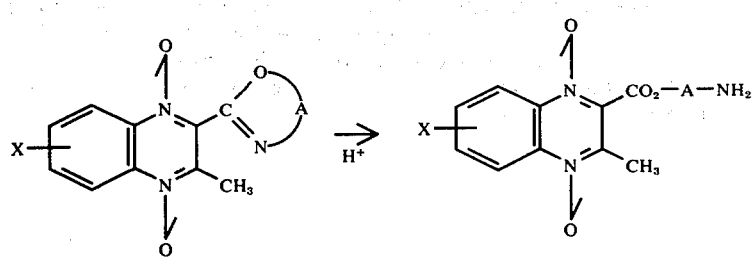

Hydrolysis of the aforementioned oxazacyclic moiety at the 2-position of the appropriate 3-methylquinoxaline-1,4-di-N-oxide is most conveniently carried out using a suitable acid, such as hydrobromic, hydrochloric, phosphoric or sulfuric in a water-water miscible solvent system such as methanol-water or ethanol-water. In general, a 2–5 fold excess of said acid is employed to facilitate the reaction. The hydrolysis is carried out at temperatures of 0°–50° C. with a preferred range of 25°–35° C. and for a reaction period of 15 minutes to 2 hours.

The workup procedure for said reaction consists of removal of excess water, solvent and acid under reduced pressure, followed by trituration of the resulting salt with a suitable solvent, such as ethyl acetate or isopropanol. It is advantageous, whenever possible, to employ the same acid for the hydrolysis as is desired as the salt of the final product. For example, if the hydrochloride salt is desired then hydrochloric acid is employed, the sulfate salt— sulfuric acid, etc.

The requisite 2-(1,3-oxazacyclic)-3-methylquinoxaline-1,4-di-N-oxides for the aforementioned hydrolysis reaction are conveniently prepared by one of two synthetic routes. The first scheme, as illustrated, consists of the

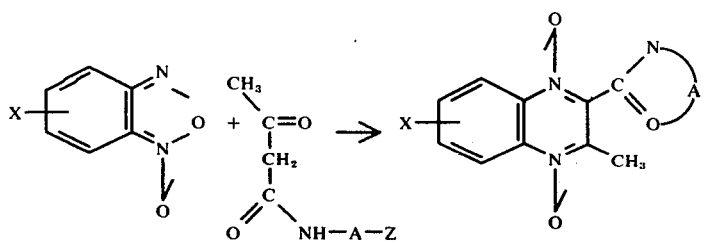

interaction of an appropriately substituted benzofuroxan with an acetoacetamide substituted on the amide nitrogen by an ω-haloalkylene moiety (Z = Cl or Br). The previously outlined reaction conditions leading to the products of the instant invention are employed with the exception that at least two molar equivalents of base are used per mole of benzofuroxan and acetoacetamide. In general, the workup procedure consists of cooling the reaction mixture and filtering the resulting product or, alternately, pouring the mixture into water followed by extraction of the product with an appropriate solvent, such as chloroform or methylene chloride.

The N-substituted acetoacetamide derivatives employed as starting materials are easily synthesized by those skilled in the art as taught by the method of D'Angeli, et al., Tetrahedron Letters, 605 (1965).

The second and alternate synthesis of the intermediate 2-(1,3-oxazacyclic)-3-methylquinoxaline-1,4-di-N-oxides comprises contacting an appropriately substituted benzofuroxan with a 2-acetonyl-1,3-oxazacyclic compound, as illustrated:

Acylation of the anion of the appropriate 2-methyl-1,3-oxazacyclic intermediate employing either ethyl acetate or acetyl chloride provides the desired 2-acetonyl derivative. In practice, the anion of the requisite 2-methyl-1,3-oxazacyclic compound generated according to the conditions as taught by Meyer, et al., J. Am. Chem. Soc., 91, 763 (1969), is treated with an equimolar amount of ethyl acetate or acetyl chloride in a suitable solvent such as tetrahydrofuran or diethyl ether at temperatures of from −30° to −50° C. When the reaction is complete, it is filtered and the solvent removed in vacuo. The desired acetonyl derivative is purified either by distillation under reduced pressure or recrystallized from a suitable solvent.

The aforementioned 2-methyl-1,3-oxazacyclic compounds necessary for the aforedescribed procedure are either readily available or easily prepared by methods known to those skilled in the art, for instance, according to the methods as outlined by Elderfield, "Heterocyclic Compounds," John Wiley and Sons, Inc., New York, 1957, Vol. 5, page 377 and Vol. 6, page 534, and by Eckstein, Adv. Heterocyclic Chem., 311 (1963).

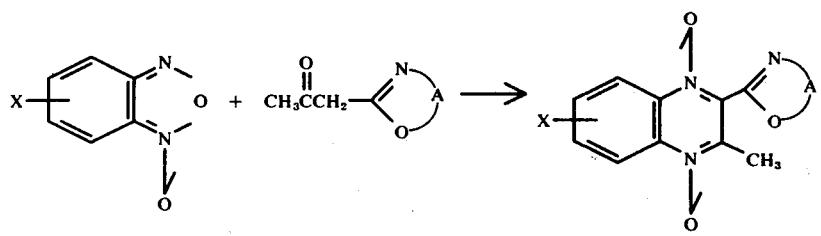

The reaction conditions, solvents and isolation leading to these compounds are the same are previously outlined for the products of the present invention.

Compounds of the instant invention where Z is a secondary amine, —NHR$_1$, wherein R$_1$ is as previously indicated, are prepared by the following sequence of reactions:

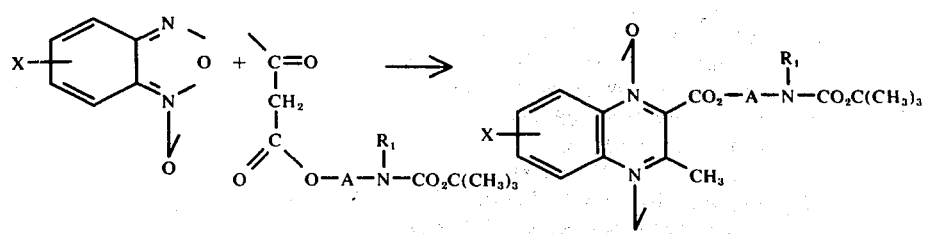

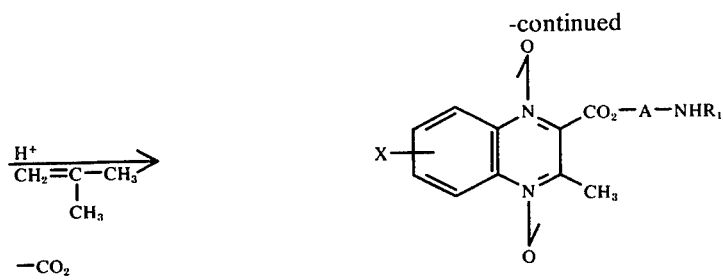

Reaction conditions, solvents and isolation procedures of the first reaction relating to the formation of the quinoxaline-di-N-oxide from the requisite benzofuroxan and acetoacetate are as previously described, as are the reaction conditions leading to the acetoacetates from diketene and the appropriate N-t-butyloxycarbonylaminoalkanol.

The aforementioned N-t-butyloxycarbonylaminoalkanols are easily prepared from the aminoalkanols and t-butyl cyanoformate by procedures known in the art; for example, by the general procedure of Leplawy, et al., *Bull. acad. polon. sci., ser. sci. chem.*, 12, 21 (1964); C. A., 61, 1933 (1964).

The second step in the sequence which relates to the removal of the t-butyl protecting group is carried out using a dilute mineral acid such as hydrochloric acid or hydrobromic acid. In practice, the 3-methyl-2-quinoxaline-carboxylic acid, N-t-butyloxycarbonylaminoalkylene ester, 1,4-dioxide in a suitable, water miscible solvent such as ethanol or methanol is treated with at least one mole equivalent of said acid and preferably a 10–50% excess. The reaction is carried out in a temperature range of 0°–50° C., with a preferred reaction temperature of 25°–35° C., and a reaction period of 30 minutes to 3 hours. A convenient method of isolation consists of removal of the solvent and excess acid under reduced pressure. The resulting salt can be further purified by recrystallization from or trituration with a suitable solvent.

In addition to the aforementioned synthetic routes to the compounds of the present invention wherein Z is acyloxy and disubstituted amino, there are three additional preparative schemes.

Scheme I encompasses the condensation of a benzofuroxan with an α- ketoester, illustrated as follows:

wherein X and A are as previously indicated, R$_4$ is alkyl containing from 1 to 3 carbon atoms and Z is acyloxy of the formula —O$_2$CR where R is hydrogen, alkyl containing from 1 to 10 carbon atoms, or benzoyl and substituted benzoyl; Z is disubstituted amino.

The reaction conditions and solvents for Scheme I are essentially those described previously for the condensation of a benzofuroxan and an acetoacetate ester, with the preferred base an alkali metal alkoxide. The workup procedure and product isolation are as previously indicated.

The α-ketoesters employed as the starting reagents for the afore-described reaction are conveniently prepared by one skilled in the art, e.g., according to the method as outlined by Vogel, et al., *Helv. Chim. Acta.*, 33 1231 (1950).

The second alternate route, Scheme II, comprises a transesterification reaction of a performed 3-alkyl(C$_1$ — C$_3$)-2-quinoxalinecarboxylic acid ester with an alkanol of the formula HO—A—Z wherein A and Z are as indicated in Scheme I, as is illustrated:

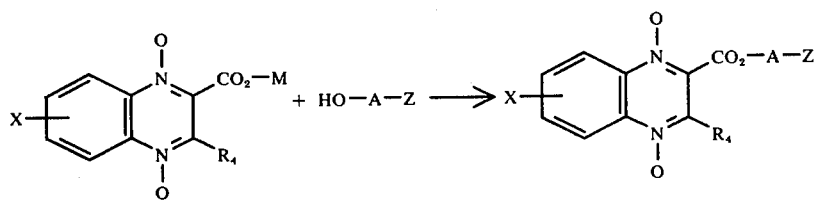

wherein X is as previously indicated and M is lower alkyl or phenyl.

In practice, the starting lower alkyl or phenyl ester is treated with at least an equimolar, and preferably a 100–200% excess of the requisite alkanol, HO—A—Z, and an acid, e.g., toluenesulfonic acid or hydrochloric acid. Said acid may be used in catalytic quantities or in as much as an equimolar amount plus a 10–20% excess. The reaction may be carried out either in a solvent such as benzene, toluene or xylene or neat, i.e., without a solvent. However, it is preferred that a solvent be used to provide a single contact phase. The reaction temperature used will vary with the reflux temperature of the solvent employed. In general, temperatures of 90°–110°

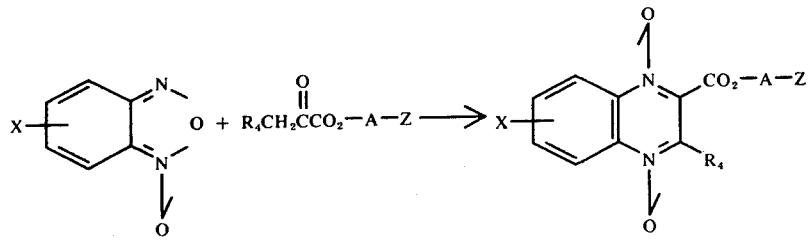

C. are adequate to effect the aforementioned reaction, with reaction times dependent on the dilution of the reaction mixture and the reactivities of the starting reagents. The products are isolated by removing the solvent in vacuo, followed by trituration or recrystallization from an appropriate solvent. The requisite 3-alkyl-2-quinoxalinecarboxylic acid esters used as a starting reagent in Scheme II are prepared according to the method of Issidorides, et al., *J. Org. Chem.*, 31, 4067 (1966).

The third alternate preparative method, Scheme III, employs the alcoholysis of the corresponding 2-cyanoquinoxaline-di-N-oxides as follows:

The reaction is subsequently quenched in water, extracted with a water immiscible solvent and the water layer acidified with concentrated hydrochloric acid to a pH of about 3. The liberated product is extracted into chloroform and the organic layer separated, dried over sodium sulfate and concentrated in vacuo to dryness. The residual product can be further purified by recrystallization from an appropriate solvent.

Acylation of the hydroxyl moiety with alkyl chloroformate esters lead to those analogs wherein Z is alkoxycarbonyloxy, and is carried out employing the appropriate hydroxyalkyl ester and a halo formate ester in a solvent such as chloroform or methylene chloride in

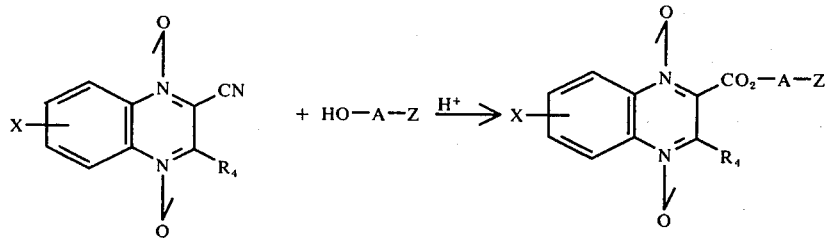

wherein X, $R_4$, A and Z are as previously indicated.

In practice, the nitrile is heated with at least an equimolar amount and as much as a 100% excess of the requisite alkanol in the presence of at least an equimolar amount plus as much as a 20% excess of an acid such as sulfuric or hydrochloric acid in a reaction-inert solvent or neat. A necessary element in the described reaction is at least an equimolar amount of water. In general, steam bath temperatures are adequate to effect said reaction. Reaction times are not critical, but will vary will temperature and the reactivity of the starting reagents.

The work-up procedure employs removal of excess alkanol in vacuo followed by trituration of the product with a suitable solvent.

The requisite 2-cyano-3-alkylquinoxaline-di-N-oxides are synthesized from the corresponding benzofuroxan and the appropriate β-ketonitrile. Said β-ketonitriles are readily accessable by methods known to those skilled in the art, e.g., according to the procedures as outlined in "Synthetic Organic Chemistry," John Wiley & Sons, Inc., New York, 1956, page 348.

Compounds of the instant invention wherein Z is carboxyacyloxy and X and A are as previously indicated are synthesized from those wherein Z is hydroxy via acylation of said hydroxy moiety employing an activated form of a dicarboxylic acid. Said activation may be through the acid halide, mixed anhydride or the simple cyclic anhydride, all in the presence of a proton acceptor such as a tertiary amine, i.e., triethyl amine. Also useful in the afore-described condensation utilizing the dicarboxylic acid and alcohol is the condensing agent carbodiimide.

In practice, the hydroxyalkyl ester of 3-methyl-2-quinoxalinecarboxylic acid 1,4-dioxide is acrylated with at least an equimolar amount, plus as much as a 100% excess of an activated dicarboxylic acid selected from the group previously enumerated. Said reaction is conducted in an aprotic solvent such as acetone, methylene chloride or chloroform. Reflux temperatures are favored, with reaction times of 2-6 hours. As previously mentioned, a proton acceptor is employed in molar amounts equivalent to the dicarboxylic acid.

the presence of a tertiary amine, e.g., pyridine or triethyl amine. Generally, it is advantageous to employ as much as a 100% excess of the halo formate and tertiary amine.

Experimentally, a solution of the hydroxyalkyl ester and tertiary amine, cooled to 0° C. is treated with the requisite halo formate. After 1-2 hours at ambient temperatures the reaction mixture is treated with a saturated sodium bicarbonate solution then washed with 6N hydrochloric acid. The solvent, containing the product, is then dried and evaporated to dryness. The product is usually triturated or recrystallized from a suitable solvent.

In a similar manner, congeners of the products of the present invention wherein Z is chloro- or bromoacyloxy and N-alkylcarbamyloxy are synthesized by contacting the requisite hydroxyalkyl ester with a chloro- or bromoacyl halide or alkylisocyanate, respectively.

Reaction of the aforementioned chloro- or bromoacyloxy compounds with at least two moles of a secondary amine in a reaction-inert solvent such as benzene, chloroform or methylene chloride at 50°-80° C. for 1-3 hours results in the preparation of those congeners wherein Z is dialkylaminoacyloxy.

These resulting tertiary amines are readily quaternarized by treatment with at least an equimolar amount of an appropriate alkylating agent, e.g., alkyl halide or alkyl sulfonate ester. Said reaction is most conveniently carried out at elevated temperatures in a reaction-inert solvent such as acetone, tetrahydrofuran or benzene. The product, which generally forms as a precipitate as the reaction proceeds, is filtered from the cooled reaction mixture and subsequently recrystallized.

An alternate, and equally effective means of preparing these quaternary salts, comprises the substitution of a tertiary amine for a secondary amine in the aforementioned reaction with compounds wherein Z is chloro- and bromoacyloxy. In said reaction, compounds of the present invention wherein Z is chloro- and bromoacyloxy dissolved in methylene chloride or chloroform are treated with at least a molar equivalent, plus as much as a 100% excess, of the appropriate trialkylamine at ice-bath temperatures for from 6-12 hours. The resulting quaternary chloride or bromide salts are conveniently isolated by filtration from the reaction mixture.

As has been previously noted, the compounds of the instant invention wherein Z is amino, mono- and disubstituted amino and dialkylaminoacyloxy can form acid addition salts wherein said acid addition salts are considered to be the full equivalent of the free bases. Basic compounds of the present invention are converted to the acid addition salts by interaction of the base with an acid either in an aqueous or non-aqueous medium. In a similar manner, treatment of the acid addition salts with an aqueous base solution, e.g., alkali metal hydroxides, alkali metal carbonates and alkali metal bicarbonates or with a metal cation which forms an insoluble precipitate with the acid anion, results in a regeneration of the free base form. Such conversions are best carried out as rapidly as possible and under temperature conditions and method dictated by the stability of said basic products. The bases thus regenerated may be reconverted to the same or a different acid addition salt.

In the utilization of the chemotherapeutic acitivity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid-addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic and gluconic.

A characteristic feature of the compounds of the present invention wherein Z is carboxyacyloxy and A and X are as previously indicated is their ability to form basic salts. Said compounds are converted to basic salts by the interaction of said acid with an appropriate base in an aqueous or non-aqueous medium. Such basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzyl-amine, p-toluidine, ethylamine, octylamine, tertiary amines such as diethyl-aniline, N-methylpyrrolidine, N-methylmorpholine and 1,5-diazabicyclo-[4,3,0]-5-nonene; sodium hydroxide, potassium hydroxide, ammonium hydroxide, sodium ethoxide, potassium methoxide, magnesium hydroxide, calcium hydride and barium hydroxide.

As previously indicated, the quinoxaline-di-N-oxides of the present invention are all readily adapted to therapeutic use as antibacterial agents and as growth promotants. Typical member compounds of interest in this series include 3-methyl-2-quinoxalinecarboxylic acid, 2-aminoethyl ester, 1,4-dioxide; 3-methyl-2-quinoxalinecarboxylic acid, 2-(dimethylamino)ethyl ester, 1,4-dioxide; 3-methyl-2-quinoxalinecarboxylic acid, 2-(methylethylamino)ethyl ester, 1,4-dioxide, 3-methyl-2-quinoxalinecarboxylic acid, 2-(acetyloxy)ethyl ester, 1,4-dioxide; 3-methyl-2-quinoxalinecarboxylic acid, 2-hydroxyethyl ester, 1,4-dioxide; 3-methyl-2-quinoxalinecarboxylic acid, 2-(3-carboxypropionyloxy)ethyl ester, 1,4-dioxide; 3-methyl-2-quinoxalinecarboxylic acid, 2-(4-carboxybutryloxy)ethyl ester, 1,4-dioxide; 3-methyl-2-quinoxalinecarboxylic acid, 2-(octanoyloxy)ethyl ester, 1,4-dioxide; 3-methyl-2-quinoxalinecarboxylic acid, 2-[(ethoxycarbonyl)oxy]ethyl ester, 1,4-dioxide; 3-methyl-2-quinoxalinecarboxylic acid, 3-(acetyloxy)propyl ester, 1,4-dioxide, 3-methyl-2-quinoxaline-carboxylic acid, 3-hydroxypropyl ester, 1,4-dioxide; 3-methyl-2-quinoxaline-carboxypyl ester, 1,4-dioxide; 3-methyl-2-quinoxaline-carboxylic acid, 1-methyl-2-hydroxyethyl ester, 1,4-dioxide; 3-methyl-2-quinoxalinecarboxylic acid, 3-(dimethylamino)propyl ester, 1,4-dioxide; 3-methyl-6- and 7-chloro-2-quinoxalinecarboxylic acid, 1-methyl-2-(diethylamino)ethyl ester, 1,4-dioxide, and 3-methyl-6- and 7-chloro-2-quinoxaline-carboxylic acid, 2-(acetyloxy)ethyl ester, 1,4-dioxide.

The valuable products of this invention are remarkably effective in treating a wide variety of pathogenic micro-organisms. They are, therefore, useful as industrial antimicrobials, for example, in water treatment, slime-control, paint preservation and wood preservation as well as for topical application purposes as disinfectants.

For in vitro use, e.g., for topical application, it will often be convenient to compound the selected product with a pharmaceutically acceptable carrier such as vegetable or mineral oil or an emollient cream. Similarly, they may be dissolved or dispersed in liquid carriers or solvents such as water, alcohol, glycols or mixtures thereof or other pharmaceutically acceptable inert media, that is, media which have no harmful effect on the active ingredient. For such purposes, it will generally be acceptable to employ concentrations of active ingredients of from about 0.01 percent to about 10 percent by weight based on total composition.

In determining the in vitro activity of an antibiotic, the sensitivity of the various micro-organisms to an antibiotic is determined by the commonly accepted two-fold serial dilution technique. Final concentrations of compound per ml. range from 100 mcg. in the first tube to 0.19 mcg. in the tenth tube. The inoculum consists of 0.5 ml. of a 1 × 10$^{-3}$ dilution of a standardized culture. Final volume in each tube or cup in the DisPoso tray is 1.0 ml. The tubes are incubated at 37° C. for approximately 24 hours. The medium used is Witkins synthetic or Brain Heart Infusion (BHI). The sensitivity (MIC — minimal inhibitory concentration) of the test organism is accepted and evidenced by the absence of gross turbidity.

Further, compounds described herein exhibit useful broad spectrum activity, that is, activity against both gram-negative and gram-positive bacteria, in contrast to the usual gram-negative activity of quinoxaline-di-N-oxides. Additionally, the compounds of the present invention are active in vivo and are especially useful as animal growth promotants, especially for swine and poultry.

When used in vivo for such purposes, these novel compounds can be administered orally or parenterally, e.g., by subcutaneous, intramuscular or intravenous injection, at a dosage of from about 1 mg./kg. to about 100 mg./kg. of body weight. Vehicles suitable for parenteral injection may be either aqueous such as water, isotonic saline, isotonic dextrose, Ringer's solution, or non-aqueous such as fatty oils of vegetable origin (cotton seed, peanut oil, corn, sesame), dimethylsulfoxide and other non-aqueous vehicles which will not interfere with therapeutic efficiency of the preparation and are nontoxic in the volume or proportion used (glycerol, propylene glycol, sorbitol and di-methylacetamide). Additionally, compositions suitable for extemporaneous preparation of solutions prior to administration may advantageously be made. such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically acceptable inert carriers including solid diluents, aqueous vehicles, nontoxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The in vivo efficacy of the compounds of the instant invention is determined by the antibacterial activity against acute infections in mice. The acute experimental infections are produced by the intraperitoneal inoculation of standardized culture suspended in either 5% hog gastric mucin or broth. A brief discussion of the words "standardized culture" would seem to be beneficial. In order to obtain reproducible results with a test compound it is necessary to control, as much as possible, the may variables that can enter into this type of test. An organism of high virulence if used in large enough numbers can make almost any drug look inactive. On the other hand, an inoculum not able to produce a measurable difference between treated and untreated groups is equally lacking in purpose.

Stock cultures of test organisms are normally maintained on slants or in liquid medium. When not routinely used they are maintained at refrigerator temperature or in a lyophilized state. When it becomes to use a culture in animal protection tests the culture is suspended in a volume of saline or broth, and the density of the suspension is measured by a photo-electric colorimeter. From this stock, ten-fold dilutions are prepared. Each dilution is inoculated into a series of mice in order to determine the $LD_{100}$, the $LD_{100}$ being the lowest concentration of organisms required to produce 100 percent deaths. For example, if it is found that a dilution of $10^{-4}$ is the lowest level of organism that will produce 100 percent death, we would probably use an inoculum of $10^{-3}$ for the drug evaluation experiments. This means that we are using about 10 $LD_{100}$ or 10 times the minimum dose required to kill mice. Such a test would also include the use of control animals which receive an inoculum of $10^{-4}$, $10^{-5}$ and possibly $10^{-6}$. These dilutions are included as a check on possible variation in virulence which can occur. Having previously determined, through the virulence titration, that $10^{-4}$ was the maximum dilution that will kill we naturally expect these animals to die, usually within 24 hours.

Each organism has its own standardized inoculum level. Some, such as Staphylococcus, may be used at $10^{-1}$, while others like Streptococcus require weekly animal passage in order to maintain virulence.

When evaluating an antibiotic for its effectiveness after a single dose, the dose is usually administered 0.5 hour after inoculating the mice with the lethal concentration of organisms. In this type of treatment schedule surviving mice are usually held for 4 days after the treatment and the percent alive is calculated.

Other methods of administration of the useful products of this invention to animals include mixing with animal feeds, the preparation of feed concentrates and supplements and dilute solutions or suspensions, e.g., a 0.1 percent solution, for drinking purposes. Surprisingly, the addition of low level amounts of the herein described quinoxaline-di-N-oxides to the diet of healthy animals, both ruminant and non-ruminant, such that these animals receive the product over an extended period of time, at a level of from about 0.1 mg./kg. to about 100 mg./kg. of body weight per day, especially over a major portion of their active growth period, results in an acceleration of the rate of growth and improves feed efficiency (the number of pounds of feed required to produce a pound gain in weight). Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed.

The herein described feed compositions have been found to be particularly valuable and outstanding in the case of swine. In some instances the degree of response may vary with respect to the sex of the animals. The products may, of course, be administered in one component of the feed or they may be blended uniformly throughout a mixed feed; alternatively as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of the quinoxaline-di-N-oxide described above. Some of the various components are commonly grains such as ground grain and grain by-products; animal protein substances, such as meat and fish by-products, vitamin-aceous mixtures, e.g., vitamin A and D mixtures, riboflavin supplements and other vitamin B complexes; and bone meal, limestone and other inorganic compounds to provide minerals.

The relative proportions of the present compounds in feeds and feed concentrates may vary somewhat, depending upon the compound, the feed with which they are employed and the animal consuming the same. These substances are advantageously combined in such relative proportions with edible carriers as to provide pre-mixes or concentrates which may readily be blended with standard nutritionally balanced feeds or which may be used themselves as an adjunct to normal feedings.

In the preparation of concentrates a wide variety of carriers, including the following: soybean oil meal, corn gluten meal, cotton seed oil meal, sunflower seed meal, linseed oil meal, cornmeal, limestone and corncob mean can be employed. The carrier facilitates uniform distribution of the active materials in the finished feed with which the concentrate is blended. The concentrate may be surface coated, if desired, with various proteinaceous materials, or edible waxes, such as zein, gelatin, microcrystalline wax and the like to provide a protective film which seals in the active ingredients. It will be appreciated that the proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e., pre-mixes, suitable for blending by feed manufacturers to produce finished feeds or concentrates of lower potency, the drug content may range from about 0.1 g. to 50 g. per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.1 to 10 g. per pound of supplement. A particularly useful concentrate is provided by blending 2 g. of drug with 1 pound of limestone or 1 pound of limestone-soybean oil meal (1:1). Other dietary supplements, such as vitamins, minerals, etc., may be added to the concentrates in the appropriate circumstances.

The concentrates described may also be added to animal feed to produce a nutritionally balanced, finished feed containing from about 5 to about 125 g. of the herein described compounds per ton of finished feed. In the case of ruminants, the finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa hay or meal, cracked corn, whole oats, soybean oil meal, corn silage, ground corn cobs, wheat bran and dried molasses. Bone meal, limestone, iodized salt and trace minerals are frequently added to supply the necessary minerals and urea to provide additional nitrogen.

As is well known to those skilled in the art, the types of diets are extremely variable, depending upon the purpose, type of feeding operation, species, etc. Specific diets for various puposes are listed by Morrison in the Appendix of "Feeds and Feeding", the Morrison Publishing Company, Clinton, Iowa, 1959.

In the case of non-ruminant animals, such as hogs, a suitable feed may contain from about 50 to 80 percent of grains, 3 to 10 percent animal protein, 5 to 30 percent vegetable protein, 2 to 4 percent of minerals, together with supplementary vitaminaceous sources.

In practice, growth promotion is determined in swine, for instance, by the method wherein young pigs from 5-6 weeks of age and averaging 21.5 lbs. initial body weight are maintained on an ad libitum consumption of water and feed formulation consisting of ground yellow corn (58.1%), soybean meal (19.6%), alfalfa meal (2.0%), dried skim milk (5.0%), dried whey (10.0%), stabilized animal fat (2.5%), limestone (0.6%), dicalcium phosphate (1.1%), iodized salt (0.5%), vitamin premix PPM5 (0.5%), quadruple delamix (0.05%), and zinc carbonate (156 g./2000 lbs. mix). The pigs are divided into groups of 32 pigs each and are held for a pre-experimental period of 3 days prior to starting the experiment. The quinoxaline-di-N-oxides of the present invention are added to the feed at a ratio of 50 g. of compound per ton of feed. After 28 days the efficacy of said added compounds on growth promotion is measured by a comparison of the growth in terms of weight gain of the treated animals with the untreated control group, which is arbitrarily assigned a weight gain Index of 100. For example, if a compound effects a growth 23% greater than the control group (with an Index of 100) it would be assigned a value of 123, etc.

The effect of a supplemented diet on the growth promotion in other species of animals using appropriate dose levels and feed formulations is assessed in an analogous manner.

The following examples are provided solely for the purpose of illustration and are not to be construed as limitations of this invention, many variations of which are possible without departing from the spirit or scope thereof.

EXAMPLE I

3-Methyl-2-quinoxalinecarboxylic acid, 2-(acetyloxy)ethyl ester, 1,4-dioxide

To a solution of 251.6 g. (1.85 moles) of benzofuroxan and 348 g. (1.85 moles) of 2-acetoxyethyl acetoacetate in 750 ml. of dimethylformamide at 50°-65° C. is added 370 ml. of a 1 M solution of sodium ethoxide in ethanol. The reaction mixture is stirred at 50° C. for 4 hours after which it is cooled, concentrated to one-half its volume and filtered. The resulting crude product is dissolved in chloroform. and the chloroform solution washed alternately with water, salt solution and water. The organic layer is separated, dried over anhydrous sodium sulfate and concentrated in vacuo to dryness. The residual solid is triturated with ether, filtered and dried, 179 g., m.p. 131°-133° C., with decomposition.

Anal. Calcd. for $C_{14}H_{14}O_6N_2$: C, 54.9; H, 4.6; N, 9.2. Found: C, 54.7; H, 4.7; N, 9.1.

EXAMPLE II

3-Methyl-6- and 7-chloro-2-quinoxalinecarboxylic Acid, 2-(acetyloxy)ethyl Ester, 1,4-dioxide To 25.5 g. (0.15 mole) of 5-chlorobenzofuroxan and 28.2 g. (0.15 mole) of 2-acetoxyethyl acetoacetate in 75 ml. of dimethylformamide at 50° C. is added dropwise 30 ml. of ethanol containing 345 mg. of reacted sodium metal. The resulting reaction mixture is allowed to stir at 50° C. for an additional 4 hours followed by the removal of the solvent under reduced pressure. The residual dark oil is dissolved in a minimum amount of chloroform and placed on a column containing 250 ml. of silica in ethyl acetate. The first 300 ml. of the eluate, benzene, is discarded and the subsequent 1.4 liters collected and concentrated to an oil. Trituration with ether results in crystallization of the desired product, which is purified by recrystallization from ethyl ether-hexane, 3.74 g.

EXAMPLE III

The procedures of Examples I and II are repeated, using equivalent amounts of the requisite starting benzofuroxans and acetoacetates, to produce the following products:

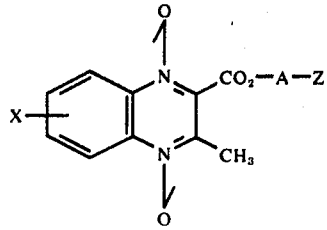

| X | A | Z |
|---|---|---|
| F | —CH₂CH₂— | HCO₂— |
| F | —CH₂CH₂— | CH₃CO₂— |
| F | —CH₂CH₂— | CH₃CH₂CO₂— |
| F | —CH₂CH₂— | (CH₃)₂CHCO₂— |
| F | —CH₂CH₂CH₂— | CH₃(CH₂)₂CO₂— |
| F | —CH₂CH₂CH₂— | CH₃CO₂— |
| F | —CH₂CH₂CH₂— | HCO₂— |
| F | —CH₂CH₂CH₂— | (CH₃)₂CHCO₂— |
| Cl | —CHCH₂—<br>    \|<br>    CH₃ | CH₃(CH₂)₂CO₂— |
| Cl | —CHCH₂—<br>    \|<br>    CH₃ | CH₃CO₂— |
| Cl | —CHCH₂—<br>    \|<br>    CH₃ | HCO₂— |
| Cl | —CHCH₂—<br>    \|<br>    CH₃ | CH₃CH₂CO₂— |
| Cl | —CH₂CH₂— | CH₃CO₂— |
| Cl | —CH₂CH₂— | HCO₂ |
| Cl | —CH₂CH₂— | CH₃CH₂CO₂— |
| Br | —(CH₂)₄— | CH₃CO₂— |
| Br | —(CH₂)₄— | HCO₂— |
| Br | —(CH₂)₄— | CH₃CH₂CO₂— |
| Br | —CH—(CH₂)₃—<br>   \|<br>   CH₃ | CH₃CO₂— |
| Br | —CH—(CH₂)₃—<br>   \|<br>   CH₃ | HCO₂— |
| Br | —CH—(CH₂)₃—<br>   \|<br>   CH₃ | (CH₃)₂CHCO₂— |
| Br | —CH₂C(CH₃)₂CH₂— | HCO₂— |
| Br | —CH₂C(CH₃)₂CH₂— | CH₃CO₂— |
| F | —CH₂C(CH₃)₂CH₂— | CH₃CH₂CO₂— |
| F | —CH₂C(CH₃)₂CH₂— | CH₃(CH₂)₂CO₂— |
| F | —CH(CH₃)CH₂CH(CH₃)— | CH₃(CH₂)₂CO₂— |
| F | —CHCH₂—<br>   \|<br>   C₂H₅ | CH₃CO₂— |
| Cl | —CHCH₂—<br>   \|<br>   C₂H₅ | CH₃CO₂— |
| Cl | —CHCH₂—<br>   \|<br>   C₃H₇ | HCO₂— |
| Cl | —CHCH₂—<br>   \|<br>   C₃H₇ | HCO₂— |
| Br | —CH(CH₂)₂—<br>   \|<br>   C₂H₅ | CH₃CO₂— |

-continued

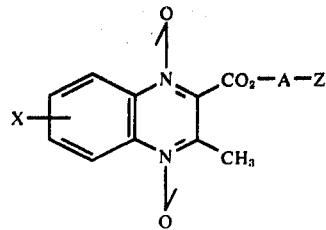

| X | A | Z |
|---|---|---|
| Br | —CH(CH₂)₂—<br>   \|<br>   C₂H₅ | HCO₂— |

EXAMPLE IV

The procedures of Examples I and II are again repeated, using the appropriately substituted benzofuroxan and acetoacetates to provide the following analogs:

| X | A | Z |
|---|---|---|
| H | —CH₂CH₂— | HCO₂— |
| H | —CH₂CH₂— | CH₃CH₂CO₂— |
| H | —CH₂CH₂— | CH₃(CH₂)₂CO₂— |
| H | —CH₂CH₂— | (CH₃)₂CHCO₂— |
| H | —(CH₂)₃ | CH₃CO₂— |
| H | —(CH₂)₃ | CH₃CH₂CO₂— |
| H | —(CH₂)₃ | HCO₂— |
| H | —CHCH₂—<br>   \|<br>   CH₃ | HCO₂— |
| H | —CHCH₂—<br>   \|<br>   CH₃ | CH₃CO₂— |
| CH₃ | —CHCH₂—<br>   \|<br>   CH₃ | CH₃CH₂CO₂— |
| CH₃ | —(CH₂)₄— | HCO₂— |
| CH₃ | —(CH₂)₄— | CH₃CO₂— |
| CH₃ | —(CH₂)₄— | (CH₃)₂CHCO₂— |
| CH₃ | —CH(CH₂)₂—<br>   \|<br>   CH₃ | (CH₃)₂CHCO₂— |
| CH₃ | —CH(CH₂)₂—<br>   \|<br>   CH₃ | CH₃CO₂— |
| CH₃ | —CH₂CH₂— | CH₃CO₂— |
| CH₃ | —CHCH₂CH—<br>   \|       \|<br>   CH₃  CH₃ | CH₃CO₂— |
| CH₃ | —CHCH₂CH—<br>   \|       \|<br>   CH₃  CH₃ | HCO₂— |

-continued

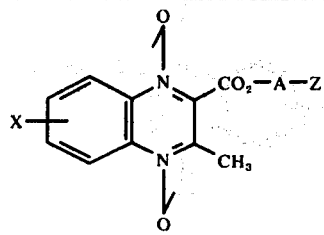

| X | A | Z |
|---|---|---|
| OCH₃ | —CHCH₂CH—<br>\|       \|<br>CH₃   CH₃ | HCO₂— |
| OCH₃ | —CH₂CH₂— | CH₃(CH₂)₂CO₂— |
| OCH₃ | —CH₂CH₂— | CH₃CO₂— |
| OCH₃ | —CH₂CH₂— | HCO₂— |
| OCH₃ | —CH(CH₂)₂—<br>\|<br>C₂H₅ | CH₃CO₂— |
| OCH₃ | —CH(CH₂)₂—<br>\|<br>C₂H₅ | HCO₂— |
| OCH₃ | —CH(CH₂)₂—<br>\|<br>C₂H₅ | (CH₃)₂CHCO₂— |
| OCH₃ | —CH₂C(CH₃)₂CH₂— | HCO₂— |
| OCH₃ | —CH₂C(CH₃)₂CH₂— | CH₃CO₂— |
| OCH₃ | —CH₂CH(C₂H₅)CH₂— | CH₃CO₂— |
| OCH₃ | —CH₂CH(C₂H₅)CH₂— | CH₃(CH₂)₂CO₂— |
| OCH₃ | —CH₂CH(C₂H₅)CH₂— | HCO₂— |
| OCH₃ | —(CH₂)₅— | CH₃CO₂— |
| CF₃ | —CH₂CH₂— | HCO₂— |
| CF₃ | —CH₂CH₂— | CH₃CO₂— |
| CF₃ | —CH₂CH₂— | CH₃(CH₂)₂CO₂— |
| CF₃ | —CH—CH₂—<br>\|<br>CH₃ | CH₃(CH₂)₂CO₂— |
| CF₃ | —CH—CH₂—<br>\|<br>CH₃ | CH₃CO₂— |
| CF₃ | —CH—CH₂—<br>\|<br>CH₃ | (CH₃)₂CHCO₂— |
| CF₃ | —(CH₂)₄— | CH₃CO₂— |
| CF₃ | —CH₂CH(CH₂)₂—<br>\|<br>CH₃ | CH₃CO₂— |

EXAMPLE V

3-Methyl-2-quinoxalinecarboxylic acid, 2-hydroxyethyl ester, 1,4-dioxide

To 100 ml. of a 12N hydrochloric acid solution is added 50 g. (0.16 mole) of 3-methyl-2-quinoxalinecarboxylic acid, 2-(acetyloxy)ethyl ester, 1,4-dioxide, and the resulting reaction mixture allowed to stir at room temperature for 1 hour. Two hundred milliliters of water and 200 ml. of chloroform are added to the mixture which is then cooled and adjusted to pH 5, using a 10% sodium hydroxide solution. The mixture is further extracted (4 × 100 ml.) with chloroform, and the combined chloroform layers dried over anhydrous sodium sulfate and concentrated to dryness under reduced pressure. The resulting residue is recrystallized from chloroform - hexane to provide the pure product as a yellow solid, 33.3 g., m.p. 146°–148° C.

Anal. Calcd. for $C_{12}H_{12}O_5N_2$: C, 54.5; H, 4.6; N, 10.6. Found: C, 54.2; H, 4.5; N, 10.7.

EXAMPLE VI

The procedure of Example V is repeated, using the appropriately substituted quinoxaline-di-N-oxides, to provide the following analogs:

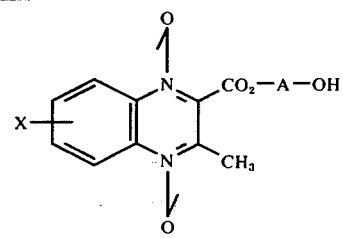

| X | A |
|---|---|
| F | —CH₂CH₂— |
| F | —CH₂CH₂CH₂— |
| F | —CH₂C(CH₃)₂CH₂— |
| F | —CF(CH₃)CH₂CH(CH₃)— |
| F | —CH(C₂H₅)CH₂— |
| Cl | —CH(CH₃)CH₂— |
| Cl | —CH₂CH₂— |
| Cl | —CH(C₂H₅)CH₂ |
| Cl | —CH(C₃H₇)CH₂— |
| Br | —(CH₂)₄— |
| Br | —CH(CH₃)(CH₂)₃— |
| Br | —CH₂C(CH₃)₂CH₂— |
| Br | —CH(C₂H₅)(CH₂)₂— |
| H | —CH₂CH₂— |
| H | —(CH₂)₃— |
| H | —CH(CH₃)CH₂— |
| CH₃ | —CH(CH₃)CH₂— |
| CH₃ | —(CH₂)₄— |
| CH₃ | —CH(CH₃)(CH₂)₂— |
| CH₃ | —CH₂CH₂— |
| CH₃ | —CH(CH₃)CH₂CH(CH₃)— |
| OCH₃ | —CH(CH₃)CH₂CH(CH₃)— |
| OCH₃ | —CH₂CH₂— |
| OCH₃ | —CH(C₂H₅)(CH₂)₂ |
| OCH₃ | —CH₂C(CH₃)₂CH₂— |
| OCH₃ | —CH₂CH(C₂H₅)CH₂— |
| OCH₃ | —(CH₂)₅— |
| CF₃ | —CH₂CH₂— |
| CF₃ | —CH(CH₃)CH₂— |
| CF₃ | —(CH₂)₄— |
| CF₃ | —CH₂CH(CH₃)(CH₂)₂— |

EXAMPLE VII

3-Methyl-2-quinoxalinacarboxylic acid, 2-aminoethyl ester, 1,4-dioxide hydrochloride To a solution of 2 ml. of water and 8 ml. of ethanol is added 0.98 ml. of 12 N hydrochloric acid (10 m.m.) followed by 1.25 g. (5 m.m.) of 2-(2-oxazolin-2-yl)-3-methylquinoxaline 1,4-dioxide. The resulting yellow solution is allowed to stir at room temperature for 30 minutes, after which it is concentrated to dryness under reduced pressure. The resulting solid is slurried in ethyl acetate and filtered, 1.26 g., m.p. 186°–188° C.

Anal. Calcd. for $C_{12}H_{14}O_4N_3Cl$: C, 48.0; H, 4.7; N, 14.0. Found: C, 47.8; H, 4.8; N, 13.9.

EXAMPLE VIII

The procedure of Example VII is repeated, using the appropriately substituted starting materials, to provide the following congeners:

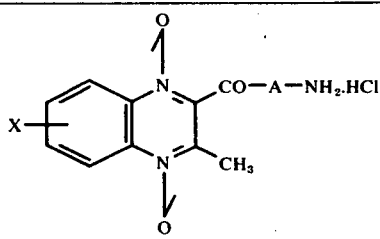

| X | A |
|---|---|
| H | —(CH₂)₃— |
| H | —CHCH₂—<br>　│<br>　CH₃ |
| H | —CH₂CH—<br>　　│<br>　　CH₃ |
| H | —(CH₂)₄— |
| H | —(CH₂)₅— |
| CH₃ | —(CH₂)₅— |
| CH₃ | —CH₂CH₂— |
| CH₃ | CH₂CHCH₂<br>　　│<br>　　C₂H₅ |
| CH₃ | —(CH₂)₃— |
| CH₃ | —CHCH₂—<br>　│<br>　C₃H₇ |
| OCH₃ | —(CH₂)₄— |
| OCH₃ | —CHCH₂CH—<br>　│　　│<br>　CH₃　CH₃ |
| OCH₃ | —CH₂CH₂— |
| OCH₃ | —(CH₂)₃— |
| OCH₃ | —CH₂C(CH₃)₂CH₂— |
| OCH₃ | —CHCH₂—<br>　│<br>　CH₃ |
| F | —CHCH₂—<br>　│<br>　CH₃ |
| F | —CH₂CH₂— |
| F | —CH₂CH—<br>　　│<br>　　CH₃ |
| F | —CH(CH₂)₃—<br>　│<br>　CH₃ |
| F | —(CH₂)₃— |
| Cl | —CH₂CH₂— |
| Cl | —CHCH₂CH—<br>　│　　│<br>　CH₃　CH₃ |
| Cl | —(CH₂)₄— |
| Cl | —(CH₂)₅— |
| Cl | —CHCH₂—<br>　│<br>　CH₃ |
| Br | —CHCH₂—<br>　│<br>　CH₃ |
| Br | —CH₂CH—<br>　　│<br>　　CH₃ |

-continued

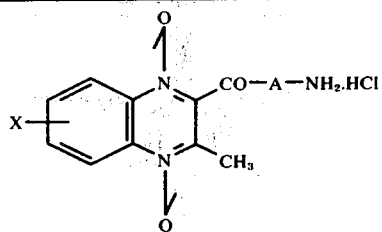

| X | A |
|---|---|
| Br | —CH₂CH—<br>　　│<br>　　C₂H₅ |
| Br | —CH₂CH₂— |
| Br | —CHCH₂—<br>　│<br>　C₃H₇ |
| CF₃ | —CHCH₂—<br>　│<br>　C₃H₇ |
| Cl | —C(CH₃)₂(CH₂)₂— |
| CF₃ | —CH₂CH₂— |
| CF₃ | —CH(CH₂)₂—<br>　│<br>　CH₃ |
| CF₃ | —CH—CH—<br>　│　　│<br>　CH₃　CH₃ |
| CF₃ | —CH—C(CH₃)₂—<br>　│<br>　CH₃ |

EXAMPLE IX

3-Methyl-2-quinoxolinecarboxylic acid, 2-(N-methylamino)-ethyl ester, 1,4-dioxide hydrochloride To 25 ml. of ethanol containing 3.8 g. (0.01 mole) of 3-methyl-2-quinoxalinecarboxylic acid, 2-(N-t-butyloxycarbonylamino)ethyl ester, 1,4-dioxide is added 1.4 ml. of a 10 M hydrochloric acid solution. The reaction mixture is heated in a water bath to 30° C. for a period of 20 minutes after which, it is concentrated to dryness under reduced pressure. The hydrochloride salt of the desired product is triturated several times with ethyl acetate and filtered.

EXAMPLE X

The procedure of Example IX is repeated, employing the requisite starting materials, to provide the following products:

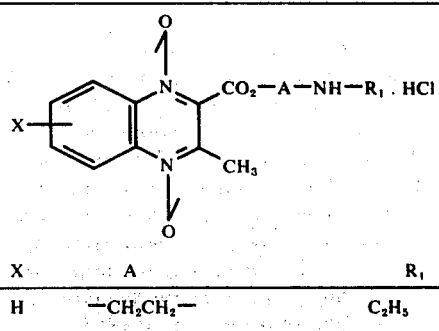

| X | A | R₁ |
|---|---|---|
| H | —CH₂CH₂— | C₂H₅ |

-continued

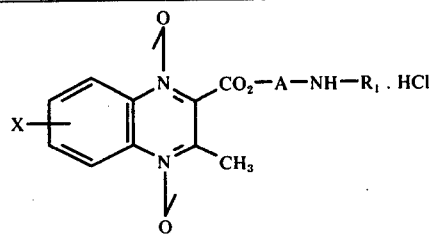

| X | A | R₁ |
|---|---|---|
| H | —CH₂CH₂— | n-C₃H₇ |
| H | —(CH₂)₃— | CH₃ |
| H | —(CH₂)₃— | C₂H₅ |
| H | —(CH₂)₃— | s-C₄H₉ |
| H | —CH(CH₃)CH₂— | C₂H₅ |
| H | —(CH₂)₄— | CH₃ |
| H | —CH₂CH(CH₃)CH₂— | n-C₄H₉ |
| H | —CH₂CH(CH₃)CH₂— | s-C₄H₉ |
| H | —(CH₂)₅— | C₂H₅ |
| H | —(CH₂)₅— | s-C₄H₉ |
| H | —CH(CH₃)(CH₂)₃— | i-C₃H₇ |
| CH₃ | —CH₂CH₂— | CH₃ |
| CH₃ | —CH₂CH₂— | C₂H₅ |
| CH₃ | —CH₂CH₂— | i-C₃H₇ |
| CH₃ | —CH₂CH(CH₃)— | C₂H₅ |
| CH₃ | —(CH₂)₄— | C₂H₅ |
| CH₃ | —CH(CH₃)(CH₂)₃— | CH₃ |
| OCH₃ | —CH₂CH₂— | CH₃ |
| OCH₃ | —CH₂CH₂— | C₂H₅ |
| OCH₃ | —CH₂CH₂— | s-C₄H₉ |
| OCH₃ | —(CH₂)₃— | n-C₄H₉ |
| OCH₃ | —(CH₂)₃— | C₂H₅ |
| OCH₃ | —(CH₂)₃— | CH₃ |
| OCH₃ | CH₂C(CH₃)₂CH₂— | CH₃ |
| OCH₃ | —(CH₂)₅— | n-C₄H₉ |

EXAMPLE XI

The procedure of Example IX is again repeated, using the appropriate starting materials, to produce the following comgeners:

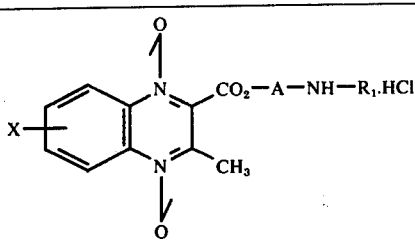

| X | A | R₁ |
|---|---|---|
| CF₃ | —CH₂CH₂— | CH₃ |
| CF₃ | —CH(CH₃)CH₂— | C₂H₅ |
| CF₃ | —(CH₂)₄— | C₂H₅ |
| CF₃ | —(CH₂)₄— | n-C₃H₇ |
| CF₃ | —(CH₂)₄— | i-C₃H₇ |
| F | —(CH₂)₄— | t-C₄H₉ |
| F | CH(CH₃)(CH₂)₂— | CH₃ |
| F | CH(CH₃)(CH₂)₂— | C₂H₅ |
| F | CH(CH₃)(CH₂)₂— | i-C₃H₇ |
| F | —CH₂CH(CH₃)CH₂— | CH₃ |
| F | —C(CH₃)₂(CH₂)₂— | CH₃ |
| F | —(CH₂)₂CH(CH₃)— | CH₃ |
| Cl | —CH₂CH₂— | CH₃ |
| Cl | —CH(CH₃)CH₂ | CH₃ |
| Cl | —CH₂CH(CH₃)— | CH₃ |
| Cl | —(CH₂)₅— | CH₃ |
| Cl | —(CH₂)₂CH(CH₃)CH₂ | CH₃ |
| Cl | —(CH₂)₂CH(CH₃)CH₂ | n-C₄H₉ |
| Cl | —C(CH₃)₂(CH₂)₂— | n-C₃H₇ |
| Cl | —CH(CH₃)(CH₂)₂— | i-C₃H₇ |
| Cl | —(CH₂)₂CH(CH₃)— | i-C₃H₇ |
| Br | —CH₂CH₂— | C₂H₅ |
| Br | —CH₂CH(CH₃)— | C₂H₅ |
| Br | —(CH₂)₂CH(CH₃)— | C₂H₅ |
| Br | —CH₂C(CH₃)₂CH₂— | C₂H₅ |
| Br | —CH(CH₃)(CH₂)₃— | C₂H₅ |

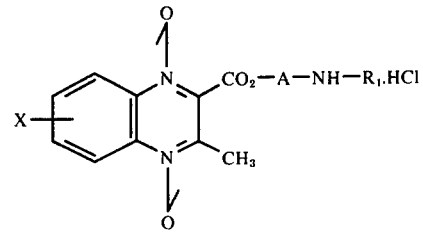

| X | A | R₁ |
|---|---|---|
| Br | —C(CH₃)₂(CH₂)₂— | C₂H₅ |

EXAMPLE XII

3-Methyl-2-quinoxalinecarboxylic acid, 2-(dimethylamino)ethyl ester, 1,4-dioxide hydrochloride To a solution of 204 g. (1.5 moles) of benzofuroxan and 259 g. (1.5 moles) of 2-(dimethylamino)ethyl acetoacetate in 600 ml. of dry dimethylformamide is added over a 15 minute period 150 ml. of 1 N sodium ethoxide in ethanol (0.15 mole). The resulting exothermic reaction raises the reaction temperature to 55° C. where it is maintained for 3 hours after the reaction subsides. The solvent is removed under reduced pressure, 1 liter of water is added and the product extracted with (5 × 200 ml.) methylene chloride. The combined methylene chloride extracts are extracted with (3 × 200 ml.) 0.5 N hydrochloric acid and the combined aqueous acid layers basified with potassium carbonate and reextracted with (4 × 200 ml.) methylene chloride. The methylene chloride extracts are combined, dried over anhydrous sodium sulfate and concentrated in vacuo to an oil. The residual oil is dissolved in 500 ml. of methanolic hydrogen chloride, and the resulting solution cooled. The desired product crystallizes as the hydrochloride salt, which is filtered, washed with ethyl acetate and dried, 138 g., m.p. 192° C. with decomposition.

Anal. Calcd. for $C_{14}H_{18}O_4N_3Cl$: C, 51.3; H, 5.5; N, 12.8. Found: C, 51.2; H, 5.7; N, 12.8.

EXAMPLE XIII

The procedure of Example XII is repeated, using appropriate starting chemicals, to provide the following products:

3-Methyl-2-quinoxalinecarboxylic acid, 1-methyl-2-(dimethyl-amino)ethyl ester, 1,4-dioxide hydrochloride; m.p. 201°-202° C. with decomposition.

3-Methyl-2-quinoxalinecarboxylic acid, 2-(methylethylamino)-ethyl ester, 1,4-dioxide hydrochloride; m.p. 185° C., with decomposition.

3-Methyl-2-quinoxalinecarboxylic acid, 2-(diethylamino)ethyl ester, 1,4-dioxide hydrochloride; m.p. 165° C., with decomposition.

3-Methyl-2-quinoxalinecarboxylic acid, 3-(dimethylamino)propyl ester, 1,4-dioxide hydrochloride; m.p. 193°-194° C., with decomposition.

3-Methyl-2-quinoxalinecarboxylic acid, 3-(diethylamino)propyl ester, 1,4-dioxide hydrochloride; m.p. 144°-145° C.

3-Methyl-2-quinoxalinecarboxylic acid, 1-methyl-2-(diethylamino)propyl ester, 1,4-dioxide; m.p. 104°-105° C.

EXAMPLE XIV

The experiment conditions of Example XII are repeated, using the requisite starting materials, to produce the following compounds:

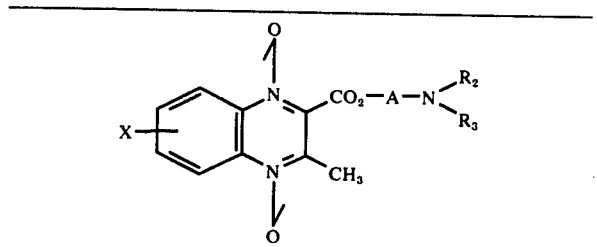

| X | A | $R_2$ | $R_3$ |
|---|---|---|---|
| F | $-CH_2CH_2-$ | $CH_3$ | $CH_3$ |
| F | $-CH_2CH_2-$ | $CH_3$ | $C_2H_5$ |
| F | $-CH_2CH_2-$ | $C_2H_5$ | $C_2H_5$ |
| F | $-CHCH_2-$<br>$\|$<br>$CH_3$ | $CH_3$ | $CH_3$ |
| F | $-CHCH_2-$<br>$\|$<br>$CH_3$ | $CH_3$ | $C_2H_5$ |
| F | $-(CH_2)_3-$ | $CH_3$ | $CH_3$ |
| Br | $-(CH_2)_3-$ | $CH_3$ | $CH_3$ |
| Br | $-(CH_2)_3-$ | $CH_3$ | $C_2H_5$ |
| Br | $-CH_2CH-$<br>$\|$<br>$CH_3$ | $CH_3$ | $C_2H_5$ |
| Br | $-CH_2CH-$<br>$\|$<br>$CH_3$ | $C_2H_5$ | $C_2H_5$ |
| Br | $-CH_2CH_2-$ | $CH_3$ | $CH_3$ |
| Br | $-CH_2CH_2-$ | $CH_3$ | $C_2H_5$ |
| Br | $-CH_2CH_2-$ | $C_2H_5$ | $C_2H_5$ |
| Br | $-(CH_2)_4-$ | $CH_3$ | $CH_3$ |
| $CF_3$ | $-(CH_2)_4-$ | $CH_3$ | $C_2H_5$ |
| $CF_3$ | $-(CH_2)_4-$ | $C_2H_5$ | $C_2H_5$ |
| $CF_3$ | $-CH_2CH_2-$ | $CH_3$ | $CH_3$ |
| $CF_3$ | $-CH_2CH_2-$ | $CH_3$ | $C_2H_5$ |
| $CF_3$ | $-(CH_2)_3-$ | $C_2H_5$ | $C_2H_5$ |
| $CF_3$ | $-(CH_2)_5-$ | $CH_3$ | $CH_3$ |
| $CF_3$ | $-(CH_2)_5-$ | $CH_3$ | $C_2H_5$ |
| $CF_3$ | $-(CH_2)_5-$ | $C_2H_5$ | $C_2H_5$ |
| $CF_3$ | $-CH_2CH-$<br>$\|$<br>$CH_3$ | $CH_3$ | $CH_3$ |
| $OCH_3$ | $-CHCH_2CH-$<br>$\|\quad\quad\|$<br>$CH_3\ \ CH_3$ | $CH_3$ | $CH_3$ |
| $OCH_3$ | $-CHCH_2CH-$<br>$\|\quad\quad\|$<br>$CH_3\ \ CH_3$ | $CH_3$ | $C_2H_5$ |
| $OCH_3$ | $-CH_2CH_2-$ | $C_2H_5$ | $C_2H_5$ |
| $OCH_3$ | $CH_2C(CH_3)_2CH_2-$ | $CH_3$ | $CH_3$ |
| $OCH_3$ | $CH_2C(CH_3)_2CH_2-$ | $CH_3$ | $C_2H_5$ |
| $OCH_3$ | $CH_2CH_2C(CH_3)_2-$ | $CH_3$ | $CH_3$ |
| $OCH_3$ | $-CH(CH_2)_2-$<br>$\|$<br>$C_2H_5$ | $CH_3$ | $CH_3$ |
| $OCH_3$ | $-CH(CH_2)_2-$<br>$\|$<br>$C_2H_5$ | $C_2H_5$ | $C_2H_5$ |
| $CH_3$ | $-CH_2CH_2-$ | $CH_3$ | $CH_3$ |
| $CH_3$ | $-CH_2CH_2-$ | $CH_3$ | $C_2H_5$ |
| $CH_3$ | $-(CH_2)_5-$ | $C_2H_5$ | $C_2H_5$ |

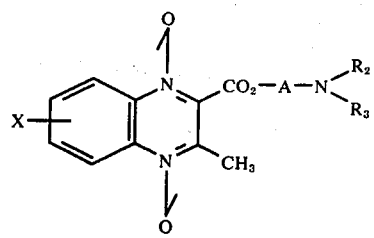

| X | A | $R_2$ | $R_3$ |
|---|---|---|---|
| $CH_3$ | $-CHCH_2-$<br>$\|$<br>$C_3H_7$ | $CH_3$ | $CH_3$ |
| $CH_3$ | $-CHCH_2-$<br>$\|$<br>$C_3H_7$ | $CH_3$ | $C_2H_5$ |
| $CH_3$ | $-CHCH_2-$<br>$\|$<br>$C_3H_7$ | $C_2H_5$ | $C_2H_5$ |
| $CH_3$ | $-(CH_2)_4-$ | $CH_3$ | $C_2H_5$ |
| $CH_3$ | $-CH(CH_2)_3-$<br>$\|$<br>$CH_3$ | $CH_3$ | $CH_3$ |

EXAMPLE XV

3-Methyl-2-quinoxalinecarboxylic acid, 2-aminoethyl ester, 1,4-dioxide hydrobromide To a solution of 3.0 g. (0.01 mole) of 3-methyl-2quinoxalinecarboxylic acid, 2-aminoethyl ester, 1,4-dioxide hydrochloride dissolved in 10 ml. of water at 0° C. is added 1.25 g. (0.005 mole) of silver oxide. The suspension is allowed to stir briefly in the cold followed by centrifugation of the solid suspension. The supernatent solution containing the free base is treated with 1.7 g. (0.01 mole) of a 48% hydrobromic acid and the resulting solution concentrated to dryness in vacuo. The resulting hydrobromide salt is triturated with ethyl acetate and suction filtered.

EXAMPLE XVI

Employing the procedure of Example XV the hydrochloride salts of the products of Example VIII are converted to their respective hydrobromide, sulfate and phosphate salts.

EXAMPLE XVII

Employing the aforementioned two-fold serial dilution technique, the in vitro activity of some of the products of the instant invention against *Staphylococcus aureus* and *Escherechia coli* are presented. Benzylpenicillin (K Salt) when tested gave MIC (Minimal Inhibitory Concentration) values of 0.156 and >100 vs. *S. aureus* and *E. coli*, respectively.

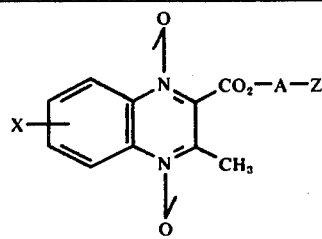

| X | A | Z | S. aureus | E. coli |
|---|---|---|---|---|
| H | $-(CH_2)_2-$ | $O-\overset{O}{\underset{\|}{C}}CH_3$ | 12.5 | 50 |
| Cl | $-(CH_2)_2-$ | $O-\overset{O}{\underset{\|}{C}}CH_3$ | 3.1 | 100 |
| H | $-(CH_2)_2-$ | $N(CH_3)_2.HCl$ | 100 | 6.25 |
| Cl | $-(CH_2)_2-$ | $N(CH_3)_2.HCl$ | 12.5 | 12.5 |
| H | $-(CH_2)_2-$ | $N(C_2H_5)_2.HCl$ | 100 | 12.5 |
| Cl | $-(CH_2)_2-$ | $N(C_2H_5)_2.HCl$ | 12.5 | 12.5 |
| H | $-(CH_2)_2-$ | $N(CH_3)C_2H_5.HCl$ | 100 | 12.5 |
| H | $-(CH_2)_3-$ | $N(C_2H_5)_2.HCl$ | 200 | 12.5 |
| H | $-CH(CH_3)CH_2-$ | $N(CH_3)_2.HCl$ | 200 | 100 |
| Cl | $-CH(CH_3)CH_2-$ | $N(CH_3)_2.HCl$ | 25 | 200 |
| H | $-(CH_2)_2-$ | $O-\overset{O}{\underset{\|}{C}}NHC_2H_5$ | 25 | >200 |

-continued

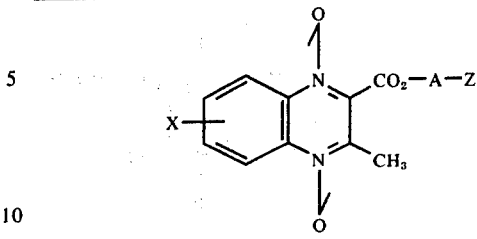

| X | A | Z | S. aureus | E. coli |
|---|---|---|---|---|
| H | $-(CH_2)_2-$ | $O-\overset{O}{\underset{\|}{C}}(CH_2)_2CO_2H$ | 200 | >200 |

EXAMPLE XVIII

Using the previously described method for determining in vivo activity, the following compounds were tested orally against *Streptococcus pyogenes* at 200 and 50 mg./kg. and against *Escherechia coli* at 100 and 25 mg./kg., unless otherwise indicated, the results being recorded as the percent animals which survived:

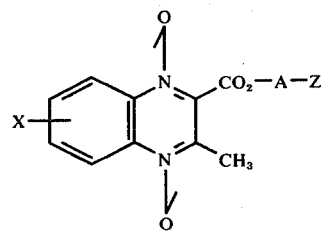

| | | | S. pyogenes | | E. coli | |
|---|---|---|---|---|---|---|
| X | A | Z | 200 | 50 | 100 | 25 |
| H | $-(CH_2)_2-$ | $-O-\overset{O}{\underset{\|}{C}}CH_3$ | 80 | 80 | 100 | 80 |
| Cl | $-(CH_2)_2-$ | $-O-\overset{O}{\underset{\|}{C}}CH_3$ | 100 | 80 | 60 | — |
| H | $-(CH_2)_2-$ | $-OH$ | 100 | 60 | 100 | 80 |
| H | $-(CH_2)_2-$ | $-NH_2.HCl$ | 90 | 30 | — | 100 |
| H | $-(CH_2)_2-$ | $N(CH_3)_2.HCl$ | 70 | 20 | 100 | 40 |
| H | $-(CH_2)_2-$ | $N(CH_3)C_2H_5.HCl$ | 100 | 60 | 80 | 0 |
| H | $-(CH_2)_3-$ | $N(CH_3)_2.HCl$ | 100 | 20 | 80 | 40 |
| H | $-CH(CH_3)CH_2-$ | $N(C_2H_5)_2.HCl$ | 80 | 20 | 60 | 0 |
| H | $-(CH_2)_2-$ | $-O-\overset{O}{\underset{\|}{C}}C_2Cl$ | — | — | 100* | 100** |
| H | $-(CH_2)_2-$ | $-O-\overset{O}{\underset{\|}{C}}C_2\overset{+}{N}(CH_3)_3Cl^-$ | — | — | 90* | 40** |
| H | $-(CH_2)_2-$ | $-O-\overset{O}{\underset{\|}{C}}NHC_2H_5$ | — | — | 30* | 40** |
| H | $-(CH_2)_2-$ | $-O-\overset{O}{\underset{\|}{C}}-C_9H_{19}$ | — | — | 100* | 70** |
| H | $-(CH_2)_2-$ | $-O-\overset{O}{\underset{\|}{C}}OC_2H_5$ | — | — | 30 | — |

-continued

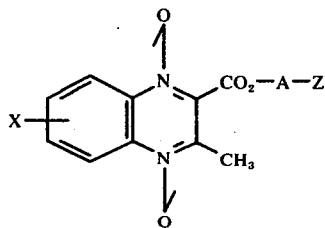

| X | A | Z | S. pyogenes 200 | S. pyogenes 50 | E. coli 100 | E. coli 25 |
|---|---|---|---|---|---|---|
| H | $-(CH_2)_2-$ | $-O-\overset{O}{\underset{\|}{C}}OCH_2CH(CH_3)_2$ | — | — | 90* | 80* |
| H | $-(CH_2)_2-$ | $-O-\overset{O}{\underset{\|}{C}}CH_2CH_3$ | — | — | 90* | 80** |
| H | $-(CH_2)_2-$ | $-O-\overset{O}{\underset{\|}{C}}(CH_2)_2CH_3$ | — | — | 90* | 80** |
| H | $-(CH_2)_2-$ | $-O-\overset{O}{\underset{\|}{C}}(CH_2)_3CH_3$ | — | — | 100* | 60** |
| H | $-(CH_2)_2-$ | $-O-\overset{O}{\underset{\|}{C}}(CH_2)_4CH_3$ | — | — | 90* | 0** |
| H | $-(CH_2)_2-$ | $-O-\overset{O}{\underset{\|}{C}}(CH_2)_5CH_3$ | — | — | 100* | 10** |
| H | $-(CH_2)_2-$ | $-O-\overset{O}{\underset{\|}{C}}(CH_2)_6CH_3$ | — | — | 100* | 50** |
| H | $-(CH_2)_2-$ | $-O-\overset{O}{\underset{\|}{C}}(CH_2)_8CH_3$ | — | — | 100* | 70** |
| H | $-(CH_2)_2-$ | $-O-\overset{O}{\underset{\|}{C}}(CH_2)_2CO_2H$ | — | — | 100* | 80** |
| H | $-(CH_2)_2-$ | $-O-\overset{O}{\underset{\|}{C}}(CH_2)_3CO_2H$ | — | — | 90* | 50** |

*200 mg./kg.
**50 mg./kg.

EXAMPLE XIX

The efficacy of the herein described compounds in protecting against a systemic challenge infection of *Salmonella cholerasuis* var. *kunzendorf* in swine is demonstrated by the following experiment. Young, 6–8 week old pigs are conditioned for 14 days in isolation rooms and maintained during the entire study on a basal ration consisting of ground yellow corn (78.4%), soybean meal (15%), alfalfa meal (2%), meat bone scraps (2.5%), limestone (0.4%), dicalcium phosphate (0.65%), iodized salt (0.5%), Vitamin pre-mix PPM5 (0.5%), quadruple delamix (0.05%) and zinc carbonate (7.8 g./100 lbs. mix). All the pigs, which are divided into groups of six, are inoculated on day 0 with 4 ml. (approximately $2.0 \times 10^8$ organisms) of the stock inoculating suspension. Treatment with the quinoxaline-di-N-oxides of the present invention is carried out on day 0 and day 1 by intramuscular injection at 12 hour intervals at doses of 2.5 and 5 mg./kg. On day 10 the percent mortality in each group is calculated. The following results are obtained:

| Medication | % Mortality |
|---|---|
| Infected, non medicated (placebo injection) | 83 |
| 3-Methyl-2-quinoxalinecarboxylic acid, 2-(acetyloxy)ethyl ester, 1,4-dioxide | |
| 2.5 mg./kg. × 4 | 67 |
| 5.0 mg./kg. × 4 | 17 |

EXAMPLE XX

Employing the previously described procedure for determining growth promotion in animals, the following quinoxaline-di-N-oxides were tested at 50 g./ton of feed in swine for a period of 28 days and provided the following results:

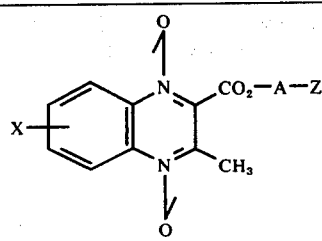

| X | A | Z | Weight Gain Index* | % Growth Over Control |
|---|---|---|---|---|
| H | $-(CH_2)_2-$ | $N(CH_3).HCl$ | 129 | 29 |
| H | $-(CH_2)_2-$ | $O-\overset{\overset{O}{\|\|}}{C}CH_3$ | 153 | 53 |
| H | $-(CH_2)_2-$ | $NH_2.HCl$ | 139 | 39 |

*control = 100

EXAMPLE XXI

The experimental procedure of Example I is repeated, using the appropriate β-ketoesters and benzofuroxans, to provide the following compounds:

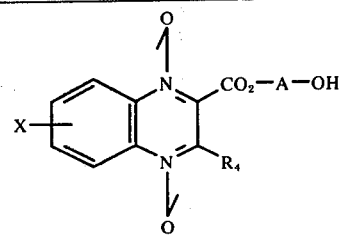

| X | $R_4$ | A |
|---|---|---|
| H | $C_2H_5$ | $-(CH_2)_2-$ |
| H | $C_3H_7$ | $-(CH_2)_2CH(CH_3)-$ |
| F | $C_2H_5$ | $-(CH_2)_4-$ |
| F | $C_3H_7$ | $-(CH_2)_2-$ |
| Cl | $C_2H_5$ | $-CH_2C(CH_3)_2CH_2-$ |
| Cl | $C_3H_7$ | $-(CH_2)_5-$ |
| Br | $C_2H_5$ | $-(CH_2)_2-$ |
| Br | $C_2H_5$ | $-(CH_2)_4-$ |
| $CH_3$ | $C_2H_5$ | $-(CH_2)_2-$ |
| $CH_3$ | $C_3H_7$ | $-(CH_2)_2-$ |
| $OCH_3$ | $C_2H_5$ | $-(CH_2)_2-$ |
| $OCH_3$ | $C_3H_7$ | $-(CH_2)_5-$ |
| $CF_3$ | $C_2H_5$ | $-(CH_3 2)_2-$ |
| $CF_3$ | $C_3H_7$ | $-CH(CH_3)CH_2CH(CH_3)-$ |

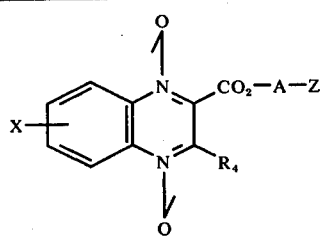

| X | $R_4$ | A | Z |
|---|---|---|---|
| H | $CH_3$ | $-(CH_2)_2-$ | $C_6H_5CO_2-$ |
| H | $CH_3$ | $-(CH_2)_4-$ | $4-(CH_3)_2NC_6H_4CO_2-$ |
| H | $C_2H_5$ | $-(CH_2)_2-$ | $CH_3CO_2-$ |
| H | $C_3H_7$ | $-(CH_2)_2CH(CH_3)-$ | $CH_3CO_2-$ |
| F | $CH_3$ | $-(CH_2)_3-$ | $4-ClC_6H_4CO_3-$ |
| F | $C_2H_5$ | $-(CH_2)_4-$ | $3-CH_3OC_6H_4CO_2-$ |
| F | $C_3H_7$ | $-(CH_2)_2-$ | $CH_3CH_2CO_2-$ |
| Cl | $CH_3$ | $-(CH_2)_2-$ | $C_6H_5CO_2-$ |
| Cl | $C_2H_5$ | $-CH_2C(CH_3)_2CH_2-$ | $CH_3CO_2-$ |
| Cl | $C_3H_7$ | $-(CH_2)_5-$ | $2-FC_6H_4CO_2-$ |
| Br | $C_2H_5$ | $-(CH_2)_2-$ | $CH_3CO_2-$ |
| Br | $C_2H_5$ | $-(CH_2)_4-$ | $CH_3CO_2-$ |
| $CH_3$ | $C_2H_5$ | $-(CH_2)_2-$ | $4-BrC_6H_4CO_2-$ |
| $CH_3$ | $C_3H_7$ | $-(CH_2)_2-$ | $CH_3CO_2-$ |
| $CH_3$ | $C_3H_7$ | $-(CH_2)_2-$ | $4-ClC_6H_4CO_2-$ |
| $OCH_3$ | $CH_3$ | $-(CH_2)_2-$ | $C_6H_5CO_2-$ |
| $OCH_3$ | $C_2H_5$ | $-(CH_2)_2-$ | $CH_3CO_2-$ |
| $OCH_3$ | $C_2H_5$ | $-(CH_2)_2-$ | $C_6H_5CO_2-$ |
| $OCH_3$ | $C_3H_7$ | $-(CH_2)_5-$ | $CH_3CO_2-$ |
| $CF_3$ | $CH_3$ | $-(CH_2)_2-$ | $C_6H_5CO_2-$ |
| $CF_3$ | $CH_3$ | $-(CH_2)_2-$ | $4-CH_3C_6H_4CO_2-$ |
| $CF_3$ | $C_2H_5$ | $-(CH_2)_2-$ | $CH_3CO_2-$ |
| $CF_3$ | $C_2H_5$ | $-(CH_2)_2-$ | $C_6H_5CO_2-$ |
| $CF_3$ | $C_3H_7$ | $-CH(CH_3)CH_2CH(CH_3)-$ | $CH_3CO_2-$ |

EXAMPLE XXII

Employing the procedure of Example V and starting with the requisite quinoxaline-di-N-oxide, the following analogs are prepared:

EXAMPLE XXIII

Starting with the appropriate quinoxaline-di-N-oxide and following the procedure of Example VII, the following congeners are prepared:

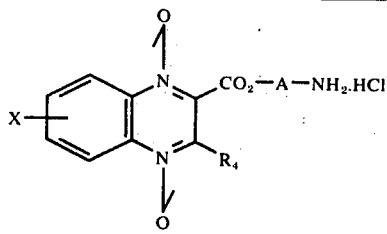

| X | R₄ | A |
|---|---|---|
| H | C₂H₅ | —(CH₂)₂— |
| H | C₂H₅ | —(CH₂)₃— |
| H | C₃H₇ | —(CH₂)₂— |
| H | C₂H₅ | —(CH₂)₃CH(CH₃)— |
| CH₃ | C₂H₅ | —(CH₂)₂— |
| CH₃ | C₃H₇ | —(CH₂)₂— |
| CH₃ | C₃H₇ | —(CH₂)₄— |
| OCH₃ | C₂H₅ | —(CH₂)₂— |
| OCH₃ | C₃H₇ | —(CH₂)₂— |
| OCH₃ | C₂H₅ | —(CH₂)₃— |
| CF₃ | C₂H₅ | —(CH₂)₂— |
| CF₃ | C₃H₇ | —CH₂CH(CH₃)— |
| CF₃ | C₃H₇ | —(CH₂)₃— |
| F | C₂H₅ | —(CH₂)₂— |
| F | C₂H₅ | —(CH₂)₃CH(CH₃)— |
| F | C₃H₇ | —(CH₂)₄— |
| Cl | C₂H₅ | —(CH₂)₂— |
| Cl | C₂H₅ | —(CH₂)₃— |
| Cl | C₃H₇ | —(CH₂)₂— |
| Br | C₃H₇ | —(CH₂)₂— |
| Br | C₃H₇ | —(CH₂)₃— |
| Br | C₃H₇ | —(CH₂)₄— |

EXAMPLE XXIV

The procedure of Example IX is again repeated, using the requisite starting material, to provide the following analogs:

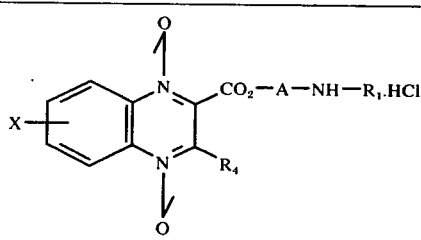

| X | R₁ | R₄ | A |
|---|---|---|---|
| H | CH₃ | C₂H₅ | —(CH₂)₂— |
| H | C₂H₅ | C₃H₇ | —(CH₂)₃— |
| H | C₂H₅ | C₂H₅ | —(CH₂)₅— |
| CH₃ | CH₃ | C₂H₅ | —(CH₂)₂— |
| CH₃ | CH₃ | C₃H₇ | —(CH₂)₂— |
| CH₃ | CH₃ | C₃H₇ | —(CH₂)₃— |
| OCH₃ | C₂H₅ | C₂H₅ | —(CH₂)₂— |
| OCH₃ | s-C₄H₉ | C₃H₇ | —(CH₂)₂— |
| OCH₃ | i-C₃H₇ | C₂H₅ | —(CH₂)₂— |
| OCH₃ | n-C₃H₇ | C₂H₅ | —(CH₂)₃— |
| CF₃ | CH₃ | C₂H₅ | —(CH₂)₂— |
| CF₃ | CH₃ | C₂H₅ | —(CH₂)₃— |
| CF₃ | CH₃ | C₂H₅ | —(CH₂)₂CH(CH₃)— |
| CF₃ | CH₃ | C₃H₇ | —(CH₂)₂— |
| F | C₂H₅ | C₂H₅ | —(CH₂)₂— |
| F | C₂H₅ | C₃H₇ | —(CH₂)₂— |
| F | C₂H₅ | C₃H₇ | —(CH₂)₃— |
| Cl | CH₃ | C₂H₅ | —(CH₂)₂— |
| Cl | CH₃ | C₂H₅ | —(CH₂)₃— |
| Cl | t-C₄H₉ | C₃H₇ | —CH(CH₃)CH₂— |
| Br | i-C₃H₇ | C₂H₅ | —(CH₂)₂— |
| Br | n-C₄H₉ | C₃H₇ | —(CH₂)₂— |

EXAMPLE XXV

The procedure of Example XII is repeated, using the appropriate starting materials, to provide the following products:

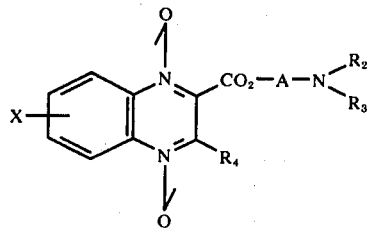

| X | A | R₄ | R₂ | R₃ |
|---|---|---|---|---|
| H | —(CH₂)₂— | C₂H₅ | CH₃ | CH₃ |
| H | —(CH₂)₂— | C₂H₅ | CH₃ | C₂H₅ |
| H | —(CH₂)₂— | C₂H₅ | C₂H₅ | C₂H₅ |
| H | —(CH₂)₃— | C₂H₅ | CH₃ | CH₃ |
| H | —(CH₂)₃— | C₂H₅ | CH₃ | C₂H₅ |
| H | —(CH₂)₄— | C₃H₇ | C₂H₅ | C₂H₅ |
| H | —(CH₂)₅— | C₃H₇ | CH₃ | CH₃ |
| CH₃ | —(CH₂)₂— | C₂H₅ | CH₃ | CH₃ |
| CH₃ | —CH(CH₃)CH₂— | C₂H₅ | CH₃ | CH₃ |
| CH₃ | —(CH₂)₃— | C₃H₇ | CH₃ | CH₃ |
| CH₃ | —(CH₂)₂CH(CH₃)— | C₂H₅ | CH₃ | C₂H₅ |
| CH₃ | —(CH₂)₅— | C₃H₇ | CH₃ | CH₃ |
| OCH₃ | —(CH₂)₂— | C₂H₅ | C₂H₅ | C₂H₅ |
| OCH₃ | —CH(CH₃)CH₂— | C₂H₅ | CH₃ | CH₃ |
| OCH₃ | —CH₂CH(CH₃)— | C₃H₇ | CH₃ | C₂H₅ |
| OCH₃ | —(CH₂)₄— | C₂H₅ | CH₃ | CH₃ |
| OCH₃ | —CH₂CH(CH₃)CH₂— | C₂H₅ | CH₃ | C₂H₅ |
| CF₃ | —(CH₂)₂— | C₃H₇ | CH₃ | CH₃ |
| CF₃ | —(CH₂)₄— | C₂H₅ | C₂H₅ | C₂H₅ |
| CF₃ | —(CH₂)₅— | C₂H₅ | CH₃ | CH₃ |
| F | —(CH₂)₂— | C₂H₅ | CH₃ | CH₃ |
| F | —CH₂CH(CH₃)— | C₂H₅ | C₂H₅ | C₂H₅ |
| F | —(CH₂)₃— | C₃H₇ | CH₃ | C₂H₅ |
| Cl | —(CH₂)₂— | C₂H₅ | CH₃ | CH₃ |
| Cl | —(CH₂)₂— | C₂H₅ | CH₃ | C₂H₅ |
| Cl | —(CH₂)₂— | C₂H₅ | C₂H₅ | C₂H₅ |
| Br | —(CH₂)₂— | C₃H₇ | CH₃ | CH₃ |
| Br | —(CH₂)₃— | C₂H₅ | CH₃ | CH₃ |
| Br | —(CH₂)₅— | C₃H₇ | C₂H₅ | C₂H₅ |

EXAMPLE XXVI

3-Methyl-2-quinoxalinecarboxylic acid, 2-(acetoxy)ethyl ester, 1,4-dioxide via Scheme I To a solution of 13.6 g. (0.1 mole) of benzofuroxan and 18.8 g. (0.1 mole) of 2-acetoxyethyl α-ketobutyrate in 150 ml. of ethanol is added 1.36 g. (0.02 mole) of sodium ethoxide. The resulting reaction mixture is stirred at 50° C. for 5 hours, and is then filtered while warm, and concentrated under reduced pressure. Cooling and scratching results in the crystallization of the desired product, which is identical to that isolated in Example I.

EXAMPLE XXVII

3-Methyl-2-quinoxalinecarboxylic acid, 2-(dimethylamino)-ethyl ester, 1,4-dioxide via Scheme II To 250 ml. of toluene is added 27.2 g. (0.2 mole) of 3-methyl-2-quinoxalinecarboxylic acid, methyl ester, 1,4-dioxide, 17.8 g. (0.2 mole) of dimethylaminoethanol and 37.8 g. (0.22 mole) of p-toluenesulfonic acid and the resulting mixture is heated to reflux. During the reaction period the reflux condenser is removed and toluene is allowed to boil off, removing methanol, the by-product of the reaction. When the reaction is complete the solvent is removed in vacuo and the residue partitioned between water and chloroform. The water layer is then separated and made slightly basic by the careful addition of a sodium hydroxide solution. The basic solution is then extracted with methylene chloride, dried over sodium sulfate and the solvent removed under reduced pressure. Addition of methanolic hydrogen chloride to the residue provides the hydrochloride of the desired product, identical to that prepared in Example XII.

EXAMPLE XXVIII

3-Methyl-2-quinoxalinecarboxylic acid, 2-(acetoxy)ethyl ester, 1,4-dioxide via Scheme III A mixture of 20.1 g. (0.1 mole) of 2-cyano-3-methyl-quinoxaline-1,4-di-N-oxide, 37.6 g. (0.2 mole) of 2-acetoxyethanol in 200 ml. of toluene is treated with 10 ml. of 12 N hydrochloric acid solution and the mixture heated at steam bath temperatures until the reaction is complete. The excess alkanol, solvent and water are removed in vacuo, and the residue is triturated several times with ether. The product isolated is identical to that prepared in Examples I and XXVI.

EXAMPLE XXIX

The procedures of Examples XXVI, XXVII and XXVIII representing Schemes I, II and III, respectively, ar repeated, using the appropriate starting reagents and reaction conditions, to provide the following quinoxaline-di-N-oxides:

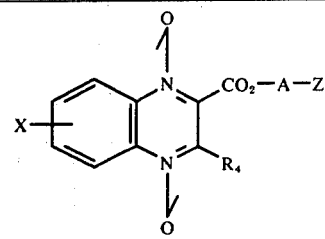

| X | R$_4$ | A | Z |
|---|---|---|---|
| H | CH$_3$ | —(CH$_2$)$_3$— | CH$_3$CO$_2$— |
| H | C$_3$H$_7$ | —(CH$_2$)$_2$— | CH$_3$CH$_2$CO$_2$— |
| H | C$_2$H$_5$ | —(CH$_2$)$_2$— | N(C$_2$H$_5$)$_2$ |
| Cl | CH$_3$ | —(CH$_2$)$_3$— | N(CH$_3$)$_2$ |
| Cl | CH$_3$ | —CH(CH$_3$)CH$_2$— | CH$_3$CO$_2$— |
| E | C$_2$H$_5$ | —(CH$_2$)$_2$— | N(CH$_3$)C$_2$H$_5$ |
| F | CH$_3$ | —(CH$_2$)$_2$— | C$_6$H$_5$CO$_2$— |
| Br | C$_3$H$_7$ | —(CH$_2$)$_2$— | N(CH$_3$)$_2$ |
| CF$_3$ | C$_2$H$_5$ | —(CH$_2$)$_2$— | CH$_3$CO$_2$— |
| CF$_3$ | C$_3$H$_7$ | —(CH$_2$)$_2$— | CH$_3$CO$_2$— |

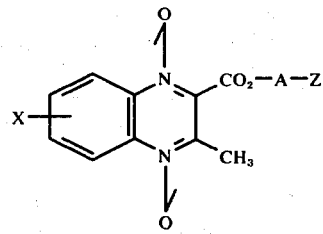

| X | R$_4$ | A | Z |
|---|---|---|---|
| CH$_3$ | C$_3$H$_7$ | —(CH$_2$)$_2$— | 4-ClC$_6$H$_4$CO$_2$— |
| OCH$_3$ | C$_3$H$_7$ | —(CH$_2$)$_5$— | CH$_3$CO$_2$— |
| OCH$_3$ | CH$_3$ | —(CH$_2$)$_2$— | C$_6$H$_5$CO$_2$— |

EXAMPLE XXX

3-Methyl-2-quinoxalinecarboxylic acid, 2-(4-carboxypropionyl-oxy)ethyl ester, 1,4-dioxide A mixture of 26.4 g. (0.1 mole) of 3-methyl-2-quinoxalinecarboxylic acid, 2-hydroxyethyl ester, 1,4-dioxide, 22 g. (0.22 mole) of succinic anhydride and 100 ml. of triethyl amine in 1 l. of acetone is heated to reflux for 2 hours and then allowed to stir at room temperature for 16 hours. The resulting reaction mixture is poured into water and extracted with chloroform (3 × 250 ml.). The aqueous phase is acidified with concentrated hydrochloric acid and the product extracted with chloroform. The organic layer is separated, dried over sodium sulfate and concentrated to an oil under reduced pressure. The residual product is induced to crystallize from methanol, 24.7 g., m.p. 165°–167° C.

Anal. Calcd. for C$_{16}$H$_{16}$O$_8$N$_2$: C, 52.8; H, 4.4; N, 7.7. Found: C, 52.9; H, 4.6; N, 7.6.

By substitution of glutaric anhydride for succinic anhydride in the above example 3-methyl-2-quinoxalinecarboxylic acid, 2-(4-carboxybutyryloxy)-ethyl ester, 1,4-dioxide, m.p. 114°–117° C., is isolated.

Anal. Calcd. for C$_{17}$H$_{18}$O$_8$N$_2$: C, 54.0; H, 4.8; N, 7.4. Found: C, 53.7; H, 4.8; N, 7.4.

EXAMPLE XXXI

Following the general procedure of Example XXX and starting with the appropriate hydroxyalkyl ester of 3-methyl-2-quinoxalinecarboxylic acid, 1,4-dioxide from Example VI and requisite anhydride or malonyl or oxalyl chloride, the following products are prepared:

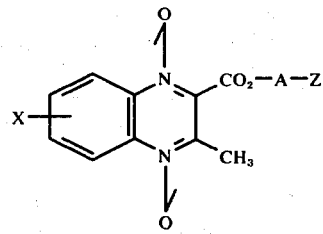

| X | A | Z |
|---|---|---|
| H | —(CH$_2$)$_2$— | —O$_2$CCH$_2$CO$_2$H |
| H | —(CH$_2$)$_2$— | —O$_2$C(CH$_2$)$_4$CO$_2$H |
| H | —(CH$_2$)$_2$— | —O$_2$C(CH$_2$)$_6$CO$_2$H |
| H | —(CH$_2$)$_3$— | —O$_2$C(CH$_2$)$_2$CO$_2$H |
| H | —CH(CH$_3$)CH$_2$— | —O$_2$CCO$_2$H |
| F | —(CH$_2$)$_2$— | —O$_2$C(CH$_2$)$_5$CO$_2$H |
| F | —CH(C$_2$H$_5$)CH$_2$— | —O$_2$CCH$_2$CO$_2$H |
| F | —(CH$_2$)$_3$— | —O$_2$C(CH$_2$)$_2$CO$_2$H |
| F | —(CH$_2$)$_3$— | —O$_2$C(CH$_2$)$_6$CO$_2$H |

-continued

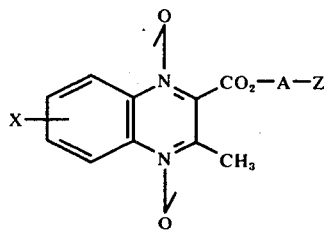

| X | A | Z |
|---|---|---|
| Cl | —CH(CH₃)CH₂— | —O₂CCH₂C(CH₃)₂CH₂CO₂H |
| Cl | —(CH₂)₂— | —O₂CCH₂C(CH₃)₂CH₂CO₂H |
| Cl | —(CH₂)₂— | —O₂C(CH₂)₄CO₂H |
| Cl | —CH(C₃H₇)CH₂— | —O₂C(CH₂)₃CO₂H |
| Br | —(CH₂)₄— | —O₂CCH(CH₃)CO₂H |
| Br | —CH₂C(CH₃)₂CH₂— | —O₂C(CH₂)₂CO₂H |
| Br | —CH₂C(CH₃)₂CH₂— | —O₂C(CH₂)₆CO₂H |
| CH₃ | —(CH₂)₂— | —O₂CCO₂H |
| CH₃ | —(CH₂)₂— | —O₂CCH₂CO₂H |
| CH₃ | —CH(CH₃)CH₂CH(CH₃)— | —O₂CCH₂CO₂H |
| CH₃ | —CH(CH₃)CH₂CH(CH₃)— | —O₂CCH₂CH(C₂H₅)CH₂CO₂H |
| OCH₃ | —(CH₂)₂— | —O₂CCH₂CH(C₂H₅)CH₂CO₂H |
| OCH₃ | —(CH₂)₂— | —O₂C(CH₂)₄CO₂H |
| OCH₃ | —(CH₂)₂— | —OC(CH₂)₃CO₂H |
| OCH₃ | —CH₂C(CH₃)₂CH₂— | —O₂C(CH₂)₆CO₂H |
| OCH₃ | —(CH₂)₅— | —O₂C(CH₂)₂CO₂H |
| CF₃ | —(CH₂)₄— | —O₂CCH(CH₃)CO₂H |
| CF₃ | —(CH₂)₄— | —O₂CCO₂H |
| CF₃ | —(CH₂)₂— | —O₂CCO₂H |
| CF₃ | —(CH₂)₂— | —O₂C(CH₂)₄CO₂H |
| CF₃ | —(CH₂)₂— | —O₂C(CH₂)₂CO₂H |

EXAMPLE XXXII

3-Methyl-2-quinoxalinecarboxylic acid, 2-(octanoyloxy)ethyl ester, 1,4-dioxide

To a solution of 26.4 g. (0.1 mole) of 3-methyl-2-quinoxalinecarboxylic acid, 2-hydroxyethyl ester, 1,4-dioxide and 30.3 g. (0.3 mole) of triethyl amine in 200 ml. of methylene chloride and cooled to 0° C., is added dropwise 32.5 g. (0.2 mole) of octanoyl chloride in 50 ml. of the same solvent. After stirring at 0° C. for 1 hour the reaction mixture is allowed to warm to room temperature and is subsequently washed with a saturated sodium bicarbonate solution and then with 6N hydrochloric acid. The organic layer is separated, dried over magnesium sulfate and evaporated in vacuo to an amber oil which is induced to crystallize with ether - petroleum ether, 25.7 g., m.p. 62°–64° C.

By replacing octanoyl chloride with the appropriate acid chloride, the following compounds are similarly prepared:

3-methyl-2-quinoxalinecarboxylic acid, 2-(propionyloxy)ethyl ester, 1,4-dioxide, m.p. 95° C.; 3-methyl-2-quinoxalinecarboxylic acid, 2-(butyryl-oxy)ethyl ester, 1,4-dioxide, m.p. 68°–69° C.; 3-methyl-2-quinoxalinecarboxylic acid, 2-(valeryloxy)ethyl ester, 1,4-dioxide, m.p. 56°–60° C.; 3-methyl-2-quinoxalinecarboxylic acid, 2-(caproyloxy)ethyl ester, 1,4-dioxide, m.p. 70°–72° C.; 3-methyl-2-quinoxalinecarboxylic acid, 2-(enanthyloxy)ethyl ester, 1,4-dioxide, m.p. 68°–70° C.; 3-methyl-2-quinoxalinecarboxylic acid, 2-(capryloxy)ethyl ester, 1,4-dioxide, m.p. 60°–62° C.; 3-methyl-2-quinoxalinecarboxylic acid, 2-(chloroacetoxy)ethyl ester, 1,4-dioxide, m.p. 115°–117° C.; 3-methyl-2-quinoxalinecarboxylic acid, 2-[(ethoxycarbonyl)oxy]ethyl ester, 1,4-dioxide; and 3-methyl-2-quinoxalinecarboxylic acid, 2-[(isobutoxycarbonyl)oxy]-ethyl ester, 1,4-dioxide, m.p. 72°–73° C.

EXAMPLE XXXIII

The procedure of Example XXXII is repeated, employing the requisite acid halides and hydroxyalkyl esters of 3-methyl-2-quinoxalinecarboxylic acid, 1,4-dioxide of Example VI, to provide the following analogs:

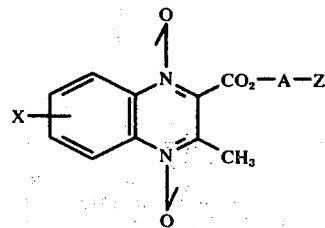

| X | A | Z |
|---|---|---|
| H | —(CH₂)₂— | —O₂CO(CH₂)₂CH₃ |
| H | —(CH₂)₂— | —O₂CCHBrCH₃ |
| H | —(CH₂)₂— | —O₂CCH₂CH₂Cl |
| H | —(CH₂)₃— | —O₂C(CH₂)₄CH₃ |
| H | —(CH₂)₃— | —O₂C(CH₂)₈CH₃ |
| H | —(CH₂)₃— | —O₂CCH₂Br |
| H | —CH(CH₃)CH₂— | —O₂CCH₂CH₂Br |
| H | —CH(CH₃)CH₂— | —O₂COC₂H₅ |
| H | —CH(CH₃)CH₂— | —O₂CO(CH₂)₃CH₃ |
| H | —CH(CH₃)CH₂— | —O₂C(CH₂)₃CH₃ |
| F | —(CH₂)₂— | —O₂C(CH₂)₄CH₃ |
| F | —(CH₂)₂— | —O₂CCHBrCH₃ |
| F | —(CH₂)₂— | —O₂C(CH₂)₂CH₂Cl |
| F | —(CH₂)₂— | —O₂COCH(CH₃)₂ |
| F | —CH₂C(CH₃)₂CH₂— | —O₂CCH₂Cl |
| F | —CH₂C(CH₃)₂CH₂— | —O₂CO(CH₂)₃CH₃ |
| F | —CH₂C(CH₃)₂CH₂— | —O₂CCH(C₂H₅)₂ |
| F | —CH₂C(CH₃)₂CH₂— | —O₂CCH(CH₃)₂ |
| Cl | —CH(C₂H₅)CH₂— | —O₂COCH₃ |
| Cl | —CH(C₂H₅)CH₂— | —O₂CCH(CH₃)CH₂Cl |
| Cl | —CH(C₂H₅)CH₂— | —O₂COCH₂CH(CH₃)₂ |
| Cl | —(CH₂)₂— | —O₂C(CH₂)₅CH₃ |
| Cl | —(CH₂)₂— | —O₂CCH(n-C₃H₇)₂ |
| Cl | —(CH₂)₂— | —O₂CCH(CH₂Cl)C₂H₅ |
| Br | —(CH₂)₄— | —O₂CCH₂Br |
| Br | —(CH₂)₄— | —O₂C(CH₂)₂CH₂Cl |
| Br | —(CH₂)₄— | —O₂CCH(CH₃)(CH₂)₅CH₃ |
| Br | —(CH₂)₄— | —O₂COC₂H₅ |

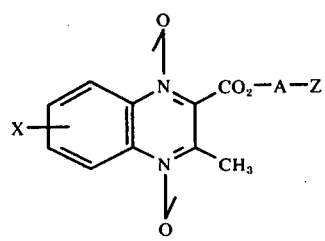

| X | A | Z |
|---|---|---|
| Br | —CH(C₂H₅)(CH₂)₂ | —O₂CCH₂CH₂Cl |
| Br | —CH(CH₃)(CH₂)₃ | —O₂COC₂H₅ |
| Br | —CH(CH₃)(CH₂)₃ | —O₂COCH(CH₃)₂ |
| CH₃ | —CH(CH₃)CH₂— | —O₂CCH₂Cl |
| CH₃ | —CH(CH₃)CH₂— | —O₂C(CH₂)₂CHCl |
| CH₃ | —CH(CH₃)CH₂— | —O₂CO(CH₂)₃CH₃ |
| CH₃ | —CH(CH₃)CH₂— | —O₂C(CH₂)₄CH₃ |
| CH₃ | —CH₂CH₂— | —O₂COC₂H₅ |
| CH₃ | —CH₂CH₂— | —O₂CCH(CH₃)CH₂Br |
| CH₃ | —CH₂CH₂— | —O₂CCHBrCH₂CH₃ |
| OCH₃ | —(CH₂)₅— | —O₂CCHClCH₃ |
| OCH₃ | —(CH₂)₅— | —O₂COCH(CH₃)₂ |
| OCH₃ | —(CH₂)₅— | —O₂C(CH₂)₇CH₃ |
| OCH₃ | —(CH₂)₅— | —O₂CCHBrCH₂CH₃ |
| OCH₃ | —CH₂CH(C₂H₅)CH₂— | —O₂CO(CH₂)₃CH₃ |
| OCH₃ | —CH₂CH(C₂H₅)CH₂— | —O₂CCHClCH₃ |
| OCH₃ | —CH₂CH(C₂H₅)CH₂— | —O₂C(CH₂)₅CH₃ |
| OCH₃ | —CH₂CH(C₂H₅)CH₂— | —O₂CCH(C₂H₅)₂ |
| CF₃ | —(CH₂)₂— | —O₂COCH₂CH(CH₃)₂ |
| CF₃ | —(CH₂)₂— | —O₂C(CH₂)₆CH₃ |
| CF₃ | —(CH₂)₂— | —O₂CCHBrCH₂CH₃ |
| CF₃ | —(CH₂)₂— | —O₂CCHCl(CH₂)₂CH₃ |
| CF₃ | —(CH₂)₂— | —O₂CO(CH₂)₃CH₃ |
| CF₃ | —(CH₂)₄— | —O₂COCH₃ |
| CF₃ | —(CH₂)₄— | —O₂CCH(CH₃)(CH₂)₆CH₃ |
| CF₃ | —(CH₂)₄— | —O₂C(CH₂)₃CH₂Br |

EXAMPLE XXXIV

3-Methyl-2-quinoxalinecarboxylic acid, 2-(N-ethylcarbamyloxy)-ethyl ester, 1,4-dioxide A solution containing 5.28 g. (0.02 mole) of 3-methyl-2-quinoxalinecarboxylic acid, 2-hydroxyethyl ester, 1,4-dioxide and 5 ml. of ethyl isocyanate in 100 ml. of dry methylene chloride is heated to 40° C. for 8 hours. The resulting reaction mixture is partitioned between water and ethyl acetate, and the organic phase separated, dried and concentrated to a yellow solid. The desired product is purified by recrystallization from chloroform - ether, 5.26 g., m.p. 116°–118° C.

Anal. Calcd. for $C_{15}H_{17}O_6N_3$: C, 53.7; H, 5.1; N, 12.5. Found: C, 53.5; H, 5.1; N, 12.3.

EXAMPLE XXXV

Starting with the appropriate 3-methyl-2-quinoxalinecarboxylic acid, hydroxyalkyl ester, 1,4-dioxide and alkyl isocyanate, and repeating the procedure of Example XXXIV, the following quinoxaline-1,4-dioxides are synthesized:

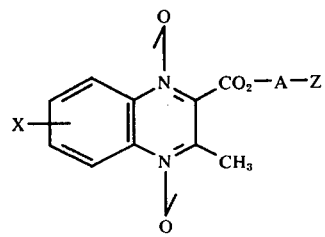

| X | A | Z |
|---|---|---|
| H | —(CH₂)₂— | —O₂CNHCH₃ |
| H | —(CH₂)₂— | —O₂CNH-n-C₃H₇ |
| H | —(CH₂)₂— | —O₂CNH-i-C₃H₇ |
| H | —(CH₂)₂— | —O₂CNHC₂H₅ |
| H | —(CH₂)₃— | —O₂CNH-n-C₄H₉ |
| H | —(CH₂)₃— | —O₂CNH-s-C₄H₉ |
| F | —CH₂C(CH₃)₂CH₂— | —O₂CNHCH₃ |
| F | —CH(C₂H₅)CH₂— | —O₂CNHCH₃ |
| F | —CH(C₂H₅)CH₂— | —O₂CNH-n-C₃H₇ |
| Cl | —CH(CH₃)CH₂— | —O₂CNH-n-C₄H₉ |
| Cl | —(CH₂)₂— | —O₂CNH-n-C₄H₉ |
| Cl | —(CH₂)₂— | —O₂CNHC₂H₅ |
| Cl | —CH(C₃H₇)CH₂— | —O₂CNH-t-C₄H₉ |
| Br | —CH(CH₃)(CH₂)₃— | —O₂CNHCH₃ |
| Br | —CH(CH₃)(CH₂)₃— | —O₂CNHC₂H₅ |
| Br | —CH(C₂H₅)(CH₂)₂— | —O₂CNH-i-C₃H₇ |
| CH₃ | —(CH₂)₄— | —O₂CNHC₂H₅ |
| CH₃ | —CH(CH₃)CH₂— | —O₂CNH-n-C₄H₉ |
| CH₃ | —CH(CH₃)CH₂— | —O₂CNH-t-C₄H₉ |
| CH₃ | —CH(CH₃)(CH₂)₂— | —O₂CNHCH₃ |
| CH₃ | —CH(CH₃)(CH₂)₂— | —O₂CNHC₂H₅ |
| OCH₃ | —CH₂C(CH₃)₂CH₂— | —O₂CNHC₂H₅ |
| OCH₃ | —CH₂C(CH₃)₂CH₂— | —O₂CNH-s-C₄H₉ |
| OCH₃ | —CH₂CH(C₂H₅)CH₂— | —O₂CNHC₂H₅ |
| OCH₃ | —(CH₂)₅— | —O₂CNHCH₃ |
| OCH₃ | —(CH₂)₅— | —O₂CNH-i-C₃H₇ |
| CF₃ | —(CH₂)₂— | —O₂CNHCH₃ |
| CF₃ | —(CH₂)₂— | —O₂CNH-s-C₄H₉ |
| CF₃ | —CH₂CH(CH₃)(CH₂)₂— | —O₂CNH-s-C₄H₉ |

EXAMPLE XXXVI

3-Methyl-2-quinoxalinecarboxylic acid, 2-(dimethylaminoacetoxy)-ethyl ester, 1,4-dioxide To a solution of 3.4 g. (0.01 mole) of 3-methyl-2-quinoxalinecarboxylic acid, 2-(chloroacetoxy)ethyl ester, 1,4-dioxide in 40 ml. of methylene chloride is added, with cooling, 1.0 g. (0.022 mole) of dimethyl amine in 10 ml. of the same solvent. The reaction mixture is allowed to stir for several hours at room temperature and is then heated to 40°–50° C. for an additional hour. The mixture is poured into water and the organic phase separated, dried over sodium sulfate and concentrated to dryness. The crude product is purified by recrystallization from chloroform - ether.

A small portion of the free base is dissolved in chloroform and sufficient hydrogen chloride dissolved in ethyl acetate added to precipitate the hydrochloride salt.

EXAMPLE XXXVII

Employing the procedure of Example XXXVI, and starting with the appropriate secondary, dialkylamine and bromo or chloro compound from Example XXXIII, the following tertiary amines are prepared:

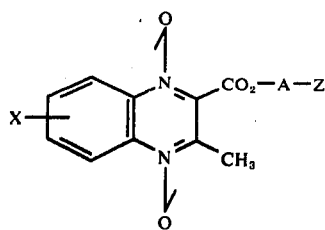

| X | A | Z |
|---|---|---|
| H | $-(CH_2)_2-$ | $-O_2CCH_2N(C_2H_5)_2$ |
| H | $-(CH_2)_2-$ | $-O_2CCH(CH_3)N(CH_3)_2$ |
| H | $-(CH_2)_3-$ | $-O_2CCH_2N(CH_3)C_2H_5$ |
| H | $-(CH_2)_3-$ | $-O_2CCH_2N(n\text{-}C_3H_7)_2$ |
| H | $-(CH_2)_3-$ | $-O_2CCH_2N(CH_3)_2$ |
| H | $-CH(CH_3)CH_2-$ | $-O_2C(CH_2)_2N(CH_3)_2$ |
| H | $-CH(CH_3)CH_2-$ | $-O_2C(CH_2)_2N(C_2H_5)_2$ |
| F | $-(CH_2)_2-$ | $-O_2CCH(CH_3)N(C_2H_5)_2$ |
| F | $-(CH_2)_2-$ | $-O_2CCH(CH_3)N(i\text{-}C_3H_7)_2$ |
| F | $-(CH_2)_2-$ | $-O_2C(CH_2)_3N(CH_3)_2$ |
| F | $-(CH_2)_2-$ | $-O_2C(CH_2)_3N(CH_3)C_2H_5$ |
| F | $-CH_2C(CH_3)_2CH_2-$ | $-O_2CCH_2N(CH_3)(n\text{-}C_3H_7)$ |
| F | $-CH_2C(CH_3)_2CH_2-$ | $-O_2CCH_2N(CH_3)_2$ |
| F | $-CH_2C(CH_3)_2CH_2-$ | $-O_2CCH_2N(n\text{-}C_3H_7)_2$ |
| Cl | $-CH(C_2H_5)CH_2-$ | $-O_2CCH(CH_3)CH_2N(CH_3)_2$ |
| Cl | $-CH(C_2H_5)CH_2-$ | $-O_2CCH(CH_3)CH_2N(C_2H_5)_2$ |
| Cl | $-(CH_2)_2-$ | $-O_2CCH(C_2H_5)CH_2N(CH_3)_2$ |
| Cl | $-(CH_2)_2-$ | $-O_2CCH(C_2H_5)CH_2N(i\text{-}C_3H_7)_2$ |
| Br | $-(CH_2)_4-$ | $-O_2CCH_2N(CH_3)C_2H_5$ |
| Br | $-(CH_2)_4-$ | $-O_2CCH_2N(C_2H_5)_2$ |
| Br | $-(CH_2)_4-$ | $-O_2C(CH_2)_3N(CH_3)_2$ |
| Br | $-CH(C_2H_5)(CH_2)_2-$ | $-O_2(CH_2)_2N(C_2H_5)_2$ |
| $CH_3$ | $-CH(CH_3)CH_2-$ | $-O_2CCH_2N(i\text{-}C_3H_7)_2$ |
| $CH_3$ | $-CH(CH_3)CH_2-$ | $-O_2CCH_2N(CH_3)(i\text{-}C_3H_7)$ |
| $CH_3$ | $-(CH_2)_2-$ | $-O_2CCH(C_2H_5)N(C_2H_5)_2$ |
| $CH_3$ | $-(CH_2)_2-$ | $-O_2CCH(CH_3)CH_2N(CH_3)_2$ |
| $OCH_3$ | $-(CH_2)_5-$ | $-O_2CCH(CH_3)N(n\text{-}C_3H_7)_2$ |
| $OCH_3$ | $-(CH_2)_5-$ | $-O_2CCH(CH_3)N(CH_3)C_2H_5$ |
| $OCH_3$ | $-(CH_2)_5-$ | $-O_2CCH(C_2H_5)N(CH_3)_2$ |
| $OCH_3$ | $-CH_2CH(C_2H_5)CH_2-$ | $-O_2CCH(CH_3)N(C_2H_5)_2$ |
| $CF_3$ | $-(CH_2)_2-$ | $-O_2CCH(C_2H_5)N(i\text{-}C_3H_7)_2$ |
| $CF_3$ | $-(CH_2)_2-$ | $-O_2CCH(n\text{-}C_3H_7)N(C_2H_5)_2$ |
| $CF_3$ | $-(CH_2)_4-$ | $-O_2C(CH_2)_4N(CH_3)_2$ |
| $CF_3$ | $-(CH_2)_4-$ | $-O_2C(CH_2)_4N(C_2H_5)_2$ |
| $CF_3$ | $-(CH_2)_4-$ | $-O_2C(CH_2)_4N(n\text{-}C_3H_7)_2$ |

EXAMPLE XXXVIII

3-Methyl-2-quinoxalinecarboxylic acid, 2-[(dimethylamino)-acetoxy]ethyl ester, 1,4-dioxide, methyl chloride

Method A

To a solution of 681 mg. (2m moles) of 3-methyl-2-quinoxalinecarboxylic acid, 2-(chloroacetoxy)ethyl, ester, 1,4-dioxide in 25 ml. of methylene chloride is introduced trimethyl amine gas with cooling (0°–10° C.) for 5 minutes. The reaction mixture, which is kept at 0° C. overnight, is filtered and the solids washed with acetone and dried, 570 mg., m.p. 85° C. The product is used without further purification.

Method B

To a solution of 3.5 g. (0.01 mole) of 3-methyl-2-quinoxalinecarboxylic acid, 2-(dimethylaminoacetoxy)ethyl ester, 1,4-dioxide in 40 ml. of cooled (0°–5° C.) methylene chloride is slowly added over a period of 15 minutes methyl chloride gas. The reaction is kept at 0° C. for several hours and is then allowed to warm to room temperature. The solid suspension is filtered, washed with acetone and oven dried. The product is identical to that prepared by the above-described Method A.

EXAMPLE XXXIX

Starting with the appropriate reagents and following the procedure of either Method A or B of Example XXXVIII, the following quaternary salts are prepared:

[Structure: quinoxaline 1,4-dioxide with X substituent, 2-position has CO₂—A—Z group, 3-position has CH₃]

| Method | X | A | Z | Anion Salt |
|---|---|---|---|---|
| A | H | —(CH₂)₂— | —O₂CCH(CH₃)N⁺(CH₃)₃ | Br⁻ |
| B | H | —(CH₂)₂— | —O₂CCH₂N⁺(CH₃)(C₂H₅)₂ | I⁻ |
| B | H | —(CH₂)₃— | —O₂CCH₂N⁺(CH₃)₂(C₂H₅) | CH₃SO₃⁻ |
| A | H | —(CH₂)₃— | —O₂CCH₂N⁺(C₂H₅)₃ | Br⁻ |
| B | F | —CH₂C(CH₃)₂CH₂— | —O₂CCH₂N⁺(CH₃)₂(n-C₃H₇) | Cl⁻ |
| B | F | —CH₂C(CH₃)₂CH₂— | —O₂CCH₂N⁺(CH₃) (n-C₃H₇)₂ | I⁻ |
| A | F | —(CH₂)₂— | —O₂C(CH₂)₃N⁺(CH₃)₃ | Cl⁻ |
| A | F | —(CH₂)₂— | —O₂C(CH₂)₃N⁺(n-C₃H₇)₃ | Cl⁻ |
| B | Cl | —CH(C₂H₅)CH₂— | —O₂CCH(CH₃)CH₂N⁺(CH₃)₃ | C₆H₅SO₃⁻ |
| A | Cl | —(CH₂)₂— | —O₂CCH(C₂H₅)CH₂N⁺(CH₃)₃ | Cl⁻ |
| A | Br | —(CH₂)₄— | —O₂CCH₂N⁺(i-C₃H₇)₃ | Br⁻ |
| B | Br | —(CH₂)₄— | —O₂C(CH₂)₃N⁺(CH₃)₂(C₂H₅) | Br⁻ |
| A | Br | —CH(C₂H₅)(CH₂)₂— | —O₂C(CH₂)₂N⁺(CH₃)₃ | Cl⁻ |
| B | CH₃ | —CH(CH₃)CH₂— | —O₂CCH₂N⁺(CH₃) (i-C₃H₇)₂ | I⁻ |
| B | CH₃ | —(CH₂)₂— | —O₂CCH(C₂H₅)N⁺(C₂H₅)₂(CH₃) | CH₃SO₃⁻ |
| A | CH₃ | —(CH₂)₂— | —O₂CCH(C₂H₅)N⁺(C₂H₅)₃ | Br⁻ |
| A | CH₃ | —CH(CH₃)CH₂— | —O₂CCH₂N⁺(n-C₃H₇)₃ | Cl⁻ |
| A | OCH₃ | —(CH₂)₅— | —O₂CCH(CH₃)N⁺(C₂H₅)₂(CH₃) | Cl⁻ |
| A | OCH₃ | —(CH₂)₅— | —O₂CCH(C₂H₅)N⁺(CH₃)₃ | Br⁻ |
| B | OCH₃ | —(CH₂)₅— | —O₂CCH(C₂H₅)N⁺(CH₃)₃ | C₆H₅SO₃⁻ |
| A | OCH₃ | —CH₂CH(C₂H₅)CH₂— | —O₂CCH(CH₃)N⁺(CH₃)₂(n-C₃H₇) | Cl⁻ |
| B | CF₃ | —(CH₂)₂— | —O₂CCH(n-C₃H₇)N⁺(C₂H₅)₂(CH₃) | I⁻ |
| B | CF₃ | —(CH₂)₂— | —O₂CCH(n-C₃H₇)N⁺(C₂H₅)₂(CH₃) | CH₃SO₃⁻ |
| B | CF₃ | —(CH₂)₂— | —O₂CCH(C₂H₅)N⁺(i-C₃H₇)₂(CH₃) | I⁻ |
| A | CF₃ | —(CH₂)₄— | —O₂C(CH₂)₄N⁺(CH₃)₃ | Br⁻ |
| A | CF₃ | —(CH₂)₄— | —O₂C(CH₂)₄N⁺(CH₃)₂(C₂H₅) | Br⁻ |
| B | CF₃ | —(CH₂)₄— | —O₂C(CH₂)₄N⁺(CH₃)₂(n-C₃H₇) | Cl⁻ |

EXAMPLE XL

3-Methyl-2-quinoxalinecarboxylic acid, 2-(3-carboxypropionyl-oxy)ethyl ester, 1,4-dioxide Sodium Salt A suspension of 728 mg. of 3-methyl-2-quinoxalinecarboxylic acid, 2-(3-carboxypropionyloxy)ethyl ester, 1,4-dioxide in 50 ml. of water is treated with one drop of phenolphthalein and then neutralized with 1N sodium hydroxide solution. The hazy solution is subsequently filtered and evaporated to dryness under reduced pressure, 665 mg., m.p. 148° C.

In a similar manner, the corresponding acids of Example XXXI are converted to their pharmaceutically acceptable basic salts.

Preparation A

Acetoacetic Acid, Alkanoyloxyalkylene Esters a. 2-(Acetyloxy)ethyl acetoacetate:

To a stirred solution of 500 g. of 2-hydroxyethyl acetate and 1 ml. of 12 M sulfuric acid is added 403 g. of diketene at such a rate that the reaction mixture temperature is maintained at 85°-105° C. When the addition is complete the mixture is heated to 110° C. for 30 minutes, and is then fractionally distilled under reduced pressure, 348 g., b.p. 154°-176° C. (18 mm).

b. General Procedure:

To the appropriate alkanoyloxyalkanol containing a catalytic amount of 12 M sulfuric acid is added, approximately, an equimolar amount of diketene at such a rate that the temperature of the resulting exothermic reaction remains at about 80°-100° C. The reaction is brought to completion by limited heating, 30–60 minutes, at 110°-115° C. The product is isolated by fractional distillation of the reaction mixture under reduced pressure.

The following compounds of the formula CH₃COCH₂CO₂—A—Z are thus prepared:

| A | Z |
|---|---|
| —CH₂CH₂— | HCO₂— |
| —CH₂CH₂— | CH₃CO₂— |
| —CH₂CH₂— | CH₃CH₂CO₂— |
| —CH₂CH₂— | CH₃(CH₂)₂CO₂— |
| —CH₂CH₂— | (CH₃)₂CHCO₂— |
| —(CH₂)₃— | HCO₂— |
| —(CH₂)₃— | CH₃CO₂— |
| —(CH₂)₃— | CH₃CH₂CO₂— |
| —(CH₂)₃— | CH₃(CH₂)₂CO₂— |
| —(CH₂)₃— | (CH₃)₂CHCO₂— |
| —CH(CH₃)CH₂— | HCO₂— |
| —CH(CH₃)CH₂— | CH₃CO₂— |
| —CH(CH₃)CH₂— | CH₃CH₂CO₂— |
| —CH(CH₃)CH₂— | CH₃(CH₂)₂CO₂— |
| —CH₂CH(CH₃)— | CH₃CO₂— |
| —(CH₂)₄— | HCO₂— |
| —(CH₂)₄— | CH₃CO₂— |
| —(CH₂)₄— | CH₃CH₂CO₂— |
| —(CH₂)₄— | (CH₃)₂CHCO₂— |
| —CH(CH₃)(CH₂)₂— | CH₃CO₂— |
| —CH(CH₃)(CH₂)₂— | (CH₃)₂CHCO₂— |
| —CH(CH₃)CH(CH₃)— | CH₃CO₂— |
| —CH(C₂H₅)CH₂— | CH₃CO₂— |
| —CH₂CH(C₂H₅)— | HCO₂— |
| —(CH₂)₅— | CH₃CO₂— |
| —CH(CH₃)(CH₂)₃— | HCO₂— |
| —CH(CH₃)(CH₂)₃— | CH₃CO₂— |
| —CH(CH₃)(CH₂)₃— | (CH₃)₂CHCO₂— |
| —CH₂CH(CH₃)(CH₂)₂— | CH₃CO₂— |
| —CH₂C(CH₃)₂CH₂— | HCO₂— |
| —CH₂C(CH₃)₂CH₂— | CH₃CO₂— |
| —CH₂C(CH₃)₂CH₂— | CH₃CH₂CO₂— |
| —CH₂C(CH₃)₂CH₂— | CH₃(CH₂)₂CO₂— |
| —CH(CH₃)CH₂CH(CH₃)— | HCO₂— |
| —CH(CH₃)CH₂CH(CH₃)— | CH₃CO₂— |
| —CH(CH₃)CH₂CH(CH₃)— | CH₃(CH₂)₂CO₂— |
| —CH(CH₃)CH(CH₃)CH₂— | CH₃CO₂— |
| —(CH₂)₂C(CH₃)₂— | CH₃CO₂— |

-continued

| A | Z |
|---|---|
| —CH(C₂H₅)(CH₂)₂— | HCO₂— |
| —CH(C₂H₅)(CH₂)₂— | CH₃CO₂— |
| —CH(C₂H₅)(CH₂)₂— | (CH₃)₂CHCO₂— |
| —CH₂CH(C₂H₅)CH₂— | HCO₂— |
| —CH₂CH(C₂H₅)CH₂— | CH₃CO₂— |
| —CH₂CH(C₂H₅)CH₂— | CH₃(CH₂)₂CO₂— |
| —CH(C₃H₇)CH₂— | HCO₂— |
| —(CH₂)₂— | C₆H₅CO₂— |
| —(CH₂)₂— | 4-CH₃C₆H₄CO₂— |
| —(CH₂)₃— | 4-ClC₆H₅CO₂— |
| —(CH₂)₄— | 4-(CH₃)₂NC₆H₄CO₂— |

Preparation B

To a solution of 8.4 g. (0.1 mole) of diketene in 150 ml. of chloroform is added 21 g. (0.11 mole) of 2-bromoethylamine hydrobromide in 30 ml. of water, and the resulting mixture stirred vigorously at 0° C. while 4.1 g. (0.11 mole) of sodium hydroxide in 20 ml. of water is added dropwise over a period of 20 minutes. The reaction mixture is allowed to stir at room temperature for 1 hour, after which the chloroform layer is separated, dried over anhydrous sodium sulfate and concentrated to dryness in vacuo to yield the intermediate, N-(2-bromoethyl)acetoacetamide, as a white crystalline residue.

The above acetoacetamide is added to 150 ml. of ethanol containing 13.6 g. (0.1 mole) of benzofuroxan followed by the addition of 16 ml. of ethylamine. The resulting mixture is allowed to stand overnight at room temperature, and is then filtered. The desired product, 2-(2-oxazolin-2-yl)-3-methylquinoxaline-1,4-dioxide, 6.4 g., m.p. 211° C., is further purified by recrystallization from methanol - chloroform, m.p. 217°-218° C.

Anal. Calcd. for C₁₂H₁₁O₃N₃: C, 58.8; H, 4.5; N, 17.1. Found: C, 58.2; H, 4.5; N, 17.0.

Starting with the appropriate bromoalkyleneamine, diketene and requisite benzofuroxan the following compounds of the formula:

Preparation C

Acetoacetic Acid, Disubstituted aminoalkylene Esters a. Acetoacetic acid, dimethylaminoethyl ester:

To a solution of 230 g. (2.6 moles) of dimethylaminoethanol and 0.5 ml. of 12 M sulfuric acid is added slowly and with external cooling 255 g. (3.0 moles) of ketene at such a rate that the reaction temperature is maintained at 55°-65° C. After the addition is complete, which requires 1 hour, the reaction mixture is allowed to cool to room temperature. Distillation of the mixture provides 371 g. of the desired product, b.p. 118°-120° C. (17 mm).

b. General Procedure:

The procedure comprises the controlled addition of diketene to the appropriate disubstitutedaminoalkanol containing a catalytic amount of sulfuric acid. Cooling and addition are adjusted so that the reaction temperature is maintained at about 50°-75° C. The product is conveniently isolated by distillation under reduced pressure.

The following compounds having the formula CH₃COCH₂CO₂—A—NR₂R₃ are thus prepared:

| A | R₂ | R₃ |
|---|---|---|
| —CH₂CH₂— | CH₃ | CH₃ |
| —CH₂CH₂— | CH₃ | C₂H₅ |
| —CH₂CH₂— | C₂H₅ | C₂H₅ |
| —(CH₂)₃— | CH₃ | CH₃ |
| —(CH₂)₃— | CH₃ | C₂H₅ |
| —(CH₂)₃— | C₂H₅ | C₂H₅ |
| —CH(CH₃)CH₂— | CH₃ | CH₃ |
| —CH(CH₃)CH₂— | CH₃ | C₂H₅ |
| —CH₂CH(CH₃)— | CH₃ | CH₃ |
| —CH₂CH(CH₃)— | CH₃ | C₂H₅ |
| —CH₂CH(CH₃)— | C₂H₅ | C₂H₅ |
| —(CH₂)₄— | CH₃ | CH₃ |

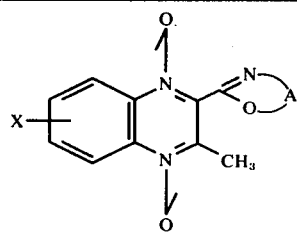

are thus prepared:

| X | A | X | A |
|---|---|---|---|
| H | —(CH₂)₃— | F | —CH(CH₃)CH₂— |
| H | —CH(CH₃)CH₂— | F | —CH₂CH₂— |
| H | —CH₂CH(CH₃)— | F | —CH₂CH(CH₃)— |
| H | —(CH₂)₄— | F | —CH(CH₃)(CH₂)₃— |
| H | —(CH₂)₅— | F | —(CH₂)₃— |
| CH₃ | —(CH₂)₅— | Cl | —CH₂CH₂— |
| CH₃ | —CH₂CH₂— | Cl | —CH(CH₃)CH₂CH(CH₃)— |
| CH₃ | —CH₂CH(C₂H₅)CH₂— | Cl | —(CH₂)₄— |
| CH₃ | —(CH₂)₃— | Cl | —(CH₂)₅— |
| CH₃ | —CH(C₃H₇)CH₂— | Cl | —C(CH₃)₂(CH₂)₂— |
| OCH₃ | —(CH₂)₄— | Cl | —CH(CH₃)CH₂— |
| OCH₃ | —CH(CH₃)CH₂CH(CH₃)— | Br | —CH(CH₃)CH₂— |
| OCH₃ | —CH₂CH₂— | Br | —CH₂CH(CH₃)— |
| OCH₃ | —(CH₂)₃— | Br | —CH₂CH(C₂H₅)— |
| OCH₃ | —CH₂C(CH₃)₂CH₂— | Br | —CH₂CH₂— |
| OCH₃ | —CH(CH₃)CH₂— | Br | —CH(C₃H₇)CH₂— |
| CF₃ | —CH(C₃H₇)CH₂— | CF₃ | —CH₂CH₂— |
| CF₃ | —CH(CH₃)(CH₂)₂— | CF₃ | —CH(CH₃)CH(CH₃)— |
| CF₃ | —CH(CH₃)C(CH₃)₂— | | |

-continued

| A | $R_2$ | $R_3$ |
|---|---|---|
| $-(CH_2)_4-$ | $CH_3$ | $C_2H_5$ |
| $-(CH_2)_4-$ | $C_2H_5$ | $C_2H_5$ |
| $-(CH_2)_5-$ | $CH_3$ | $CH_3$ |
| $-(CH_2)_5-$ | $CH_3$ | $C_2H_5$ |
| $-(CH_2)_5-$ | $C_2H_5$ | $C_2H_5$ |
| $-CH(CH_3)(CH_2)_3-$ | $CH_3$ | $CH_3$ |
| $-CH(C_2H_5)(CH_2)_2-$ | $CH_3$ | $CH_3$ |
| $-CH(C_2H_5)(CH_2)_2-$ | $C_2H_5$ | $C_2H_5$ |
| $-CH(C_3H_7)CH_2-$ | $CH_3$ | $CH_3$ |
| $-CH(C_3H_7)CH_2-$ | $CH_3$ | $C_2H_5$ |
| $-CH(C_3H_7)CH_2-$ | $C_2H_5$ | $C_2H_5$ |
| $-CH(CH_3)CH_2CH(CH_3)-$ | $CH_3$ | $CH_3$ |
| $-CH(CH_3)CH_2CH(CH_3)-$ | $CH_3$ | $C_2H_5$ |
| $-CH_2C(CH_3)_2CH_2-$ | $CH_3$ | $CH_3$ |
| $-CH_2C(CH_3)_2CH_2-$ | $CH_3$ | $C_2H_5$ |
| $-(CH_2)_2C(CH_3)_2-$ | $CH_3$ | $C_2H_5$ |

Preparation D

To a solution of 136 g. (1.0 mole) of benzofuroxan and 259.3 g. (1.0 mole) of 2-(N-methyl-N-t-butyloxycarbonylamino)ethyl acetoacetate in 750 ml. of ethanol is added 200 ml. of a 1 M solution of sodium ethoxide in ethanol. The reaction mixture is allowed to stir at 40°–50° C. for 4 hours after which it is cooled and the precipitated solid filtered and dried. The product, 3-methyl-2-quinoxalinecarboxylic acid, 2-(N-methyl-N-t-butyloxycarbonylamino)ethyl ester, 1,4-dioxide, is further purified by recrystallization from ethanol.

Starting with the appropriately substituted benzofuroxan and 2-(N-substituted N-t-butyloxycarbonylamino)alkyl acetoacetate compounds of the formula

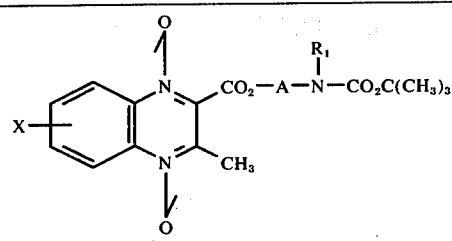

are thus prepared:

| X | A | $R_1$ |
|---|---|---|
| H | $-CH_2CH_2-$ | $C_2H_5$ |
| H | $-CH_2CH_2-$ | $n-C_3H_7$ |
| H | $-(CH_2)_3-$ | $CH_3$ |
| H | $-(CH_2)_3-$ | $C_2H_5$ |
| H | $-(CH_2)_3-$ | $s-C_4H_9$ |
| H | $-CH(CH_3)CH_2-$ | $C_2H_5$ |
| H | $-(CH_2)_4-$ | $CH_3$ |
| H | $-CH_2CH(CH_3)CH_2-$ | $n-C_4H_9$ |
| H | $-CH_2CH(CH_3)CH_2-$ | $s-C_4H_9$ |
| H | $-(CH_2)_5-$ | $C_2H_5$ |
| H | $-(CH_2)_5-$ | $s-C_4H_9$ |
| H | $-CH(CH_3)(CH_2)_3-$ | $i-C_3H_7$ |
| $CH_3$ | $-CH_2CH_2-$ | $CH_3$ |
| $CH_3$ | $-CH_2CH_2-$ | $C_2H_5$ |
| $CH_3$ | $-CH_2CH_2-$ | $i-C_3H_7$ |
| $CH_3$ | $-CH_2CH(CH_3)-$ | $C_2H_5$ |
| $CH_3$ | $-(CH_2)_4-$ | $CH_3$ |
| $CH_3$ | $-CH(CH_3)(CH_2)_3-$ | $CH_3$ |
| $OCH_3$ | $-CH_2CH_2-$ | $CH_3$ |
| $OCH_3$ | $-CH_2CH_2-$ | $C_2H_5$ |
| $OCH_3$ | $-CH_2CH_2-$ | $s-C_4H_9$ |
| $OCH_3$ | $-(CH_2)_3-$ | $n-C_4H_9$ |
| $OCH_3$ | $-(CH_2)_3-$ | $C_2H_5$ |
| $OCH_3$ | $-(CH_2)_3-$ | $CH_3$ |
| $OCH_3$ | $-CH_2C(CH_3)_2CH_2-$ | $CH_3$ |
| $OCH_3$ | $-(CH_2)_5-$ | $N-C_4H_9$ |
| $CF_3$ | $-CH_2CH_2-$ | $CH_3$ |
| $CF_3$ | $-CH(CH_3)CH_2-$ | $C_2H_5$ |
| $CF_3$ | $-(CH_2)_4-$ | $C_2H_5$ |
| $CF_3$ | $-(CH_2)_4-$ | $n-C_3H_7$ |
| $CF_3$ | $-(CH_2)_4-$ | $i-C_3H_7$ |

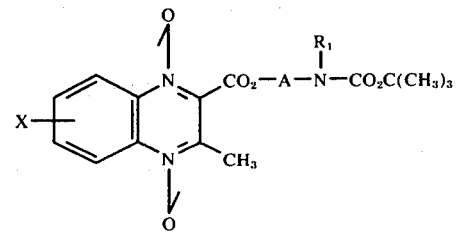

are thus prepared:

| X | A | $R_1$ |
|---|---|---|
| F | $-(CH_2)_4-$ | $t-C_4H_9$ |
| F | $-CH(CH_3)(CH_2)_2-$ | $CH_3$ |
| F | $-CH(CH_3)(CH_2)_2-$ | $C_2H_5$ |
| F | $-CH(CH_3)(CH_2)_2-$ | $i-C_3H_7$ |
| F | $-CH_2CH(CH_3)CH_2-$ | $CH_3$ |
| F | $-C(CH_3)_2(CH_2)_2-$ | $CH_3$ |
| F | $-(CH_2)_2CH(CH_3)-$ | $CH_3$ |
| Cl | $-CH_2CH_2-$ | $CH_3$ |
| Cl | $-CH(CH_3)CH_2-$ | $CH_3$ |
| Cl | $-CH_2CH(CH_3)-$ | $CH_3$ |
| Cl | $-(CH_2)_5-$ | $CH_3$ |
| Cl | $-(CH_2)_2CH(CH_3)CH_2-$ | $CH_3$ |
| Cl | $-(CH_2)_2CH(CH_3)CH_2-$ | $n-C_4H_9$ |
| Cl | $-C(CH_3)_2(CH_2)_2-$ | $n-C_3H_7$ |
| Cl | $-CH(CH_3)(CH_2)_2-$ | $i-C_3H_7$ |
| Cl | $-(CH_2)_2CH(CH_3)-$ | $i-C_3H_7$ |
| Br | $-CH_2CH_2-$ | $C_2H_5$ |
| Br | $-CH_2CH(CH_3)-$ | $C_2H_5$ |
| Br | $-(CH_2)_2CH(CH_3)-$ | $C_2H_5$ |
| Br | $-CH_2C(CH_3)_2CH_2-$ | $C_2H_5$ |
| Br | $-CH(CH_3)(CH_2)_3-$ | $C_2H_5$ |
| Br | $-C(CH_3)_2(CH_2)_2-$ | $C_2H_5$ |

Preparation E

To 84 g. (1.0 mole) of diketene contained in a three-necked round-bottom flask fitted with a mechanical stirrer addition funnel and reflux condenser and heated to 50° C. is added 500 mg. of sodium acetate followed by 175.2 g. (1.0 mole) of N-methyl-N-t-butyloxycarbonylethanolamine over a period of 20–30 minutes. The reaction mixture is allowed to stir at room temperature for 1 hour, after which it is distilled under reduced pressure to provide the desired product, 2-(N-methyl-N-t-butyloxycarbonylamino)ethyl acetoacetate.

Starting with diketene and the requisite N-substituted-N-t-butyloxy-carbonylaminoalkanol, the following compounds of the formula

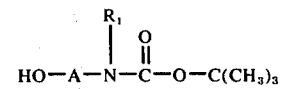

are thus prepared:

| A | $R_1$ |
|---|---|
| $-(CH_2)_2-$ | $C_2H_5$ |
| $-(CH_2)_2-$ | $i-C_3H_7$ |
| $-(CH_2)_2-$ | $n-C_3H_7$ |
| $-(CH_2)_2-$ | $s-C_4H_9$ |
| $-(CH_2)_3-$ | $CH_3$ |
| $-(CH_2)_3-$ | $C_2H_5$ |
| $-(CH_2)_3-$ | $n-C_4H_9$ |
| $-(CH_2)_3-$ | $s-C_4H_9$ |
| $-CH(CH_3)CH_2-$ | $CH_3$ |
| $-CH(CH_3)CH_2-$ | $C_2H_5$ |
| $-CH(CH_3)CH_2-$ | $n-C_3H_7$ |
| $-CH_2CH(CH_3)-$ | $CH_3$ |
| $-CH_2CH(CH_3)-$ | $C_2H_5$ |
| $-(CH_2)_4-$ | $CH_3$ |
| $-(CH_2)_4-$ | $C_2H_5$ |
| $-(CH_2)_4-$ | $n-C_3H_7$ |
| $-(CH_2)_4-$ | $i-C_3H_7$ |
| $-(CH_2)_4-$ | $t-C_4H_9$ |
| $-CH(CH_3)(CH_2)_2-$ | $CH_3$ |

-continued

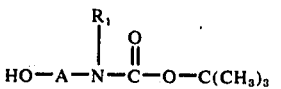

are thus prepared:

| A | R₁ |
|---|---|
| —CH(CH₃)(CH₂)₂— | C₂H₅ |
| —CH(CH₃)(CH₂)₂— | i-C₃H₇ |
| —CH₂CH(CH₃)CH₂— | CH₃ |
| —CH₂CH(CH₃)CH₂— | n-C₄H₉ |
| —CH₂CH(CH₃)CH₂— | s-C₄H₉ |
| —(CH₂)₂CH(CH₃)— | CH₃ |
| —(CH₂)₂CH(CH₃)— | C₂H₅ |
| —(CH₂)₂CH(CH₃)— | i-C₃H₇ |
| —(CH₂)₅— | CH₃ |
| —(CH₂)₅— | C₂H₅ |
| —(CH₂)₅— | s-C₄H₉ |
| —(CH₂)₅— | n-C₄H₉ |
| —(CH₂)₂CH(CH₃)CH₂— | CH₃ |
| —(CH₂)₂CH(CH₃)CH₂— | n-C₄H₉ |
| —CH₂C(CH₃)₂CH₂— | CH₃ |
| —CH₂C(CH₃)₂CH₂— | C₂H₅ |
| —CH(CH₃)(CH₂)₃— | CH₃ |
| —CH(CH₃)(CH₂)₃— | C₂H₅ |
| —CH(CH₃)(CH₂)₃— | i-C₃H₇ |
| —C(CH₃)₂(CH₂)₂— | CH₃ |
| —C(CH₃)₂(CH₂)₂— | C₂H₅ |
| —C(CH₃)₂(CH₂)₂— | n-C₃H₇ |

Preparation F

Alkanoylalkanol

The following acyloxyalkanols not previously reported in the literature are synthesized according to the method of Gibson, et al., U.S. Pat. No. 1,877,847, which comprises heating a glycol with an appropriate amide in the presence of zinc chloride under reduced pressure until such time as the evolution of ammonia has ceased.

| HO—A—Z | |
|---|---|
| A | Z |
| —CH₂CH₂— | (CH₃)₂CHCO₂— |
| —(CH₂)₃— | HCO₂— |
| —(CH₂)₃— | CH₃CO₂— |
| —(CH₂)₃— | CH₃CH₂CO₂— |
| —(CH₂)₃— | CH₃(CH₂)₂CO₂— |
| —(CH₂)₃— | (CH₃)₂CHCO₂— |
| —CH(CH₃)CH₂— | CH₃CH₂CO₂— |
| —(CH₂)₄— | HCO₂— |
| —(CH₂)₄— | CH₃CH₂CO₂— |
| —(CH₂)₄— | (CH₃)₂CHCO₂— |
| —CH(C₂H₅)CH₂— | CH₃CO₂— |
| —CH₂CH(C₂H₅)— | HCO₂— |
| —(CH₂)₅— | CH₃CO₂— |
| —CH(CH₃)(CH₂)₃— | HCO₂— |
| —CH(CH₃)(CH₂)₃— | (CH₃)₂CHCO₂— |
| —CH₂CH(CH₃)(CH₂)₂— | CH₃CO₂ |
| —CH₂C(CH₃)₂CH₂— | HCO₂— |
| —CH₂C(CH₃)₂CH₂— | CH₃CH₂CO₂— |
| —CH₂C(CH₃)₂CH₂— | CH₃(CH₂)₂CO₂— |
| —CH(CH₃)CH₂CH(CH₃)— | HCO₂— |
| —CH(CH₃)CH₂CH(CH₃)— | CH₃CO₂— |
| —CH(CH₃)CH₂CH(CH₃)— | CH₃(CH₂)₂CO₂— |
| —CH(CH₃)CH(CH₃)CH₂— | CH₃CO₂— |
| —(CH₂)₂C(CH₃)₂— | CH₃CO₂— |
| —CH(C₂H₅)(CH₂)₂— | HCO₂— |
| —CH(C₂H₅)(CH₂)₂— | CH₃CO₂— |
| —CH(C₂H₅)(CH₂)₂— | (CH₃)₂CHCO₂— |
| —CH₂CH(C₂H₅)CH₂— | HCO₂— |
| —CH₂CH(C₂H₅)CH₂— | CH₃CO₂— |
| —CH₂CH(C₂H₅)CH₂— | CH₃(CH₂)₂CO₂— |
| —CH(C₃H₇)CH₂— | HCO₂— |

Preparation G

Aminoalkanols

The following mono- and disubstituted aminoalkanols not previously described in the literature are prepared by the method of Kuznetsov, et al., Zhur. Obshchei Khim., 31, 2289 (1961) which comprises condensing a haloalkanol with a 2–5 fold excess of an appropriate amine in a sealed ampul, to provide the desired products in 30–70% yields.

| HO—A—Z | |
|---|---|
| A | Z |
| —(CH₂)₃— | NHC₂H₅ |
| —(CH₂)₃— | NH-s-C₄H₉ |
| —(CH₂)₃— | N(CH₃)C₂H₅ |
| —CH(CH₃)CH₂— | NH-n-C₃H₇ |
| —CH₂CH(CH₃)— | NHC₂H₅ |
| —CH₂CH(CH₃)— | N(CH₃)C₂H₅ |
| —(CH₂)₄— | NH-t-C₄H₉ |
| —(CH₂)₄— | N(CH₃)C₂H₅ |
| —CH(CH₃)(CH₂)₂— | NHCH₃ |
| —CH(CH₃)(CH₂)₂— | NHC₂H₅ |
| —CH(CH₃)(CH₂)₂— | NH-i-C₃H₇ |
| —CH₂CH(CH₃)CH₂— | NHCH₃ |
| —CH₂CH(CH₃)CH₂— | NH-n-C₄H₉ |
| —CH₂CH(CH₃)CH₂— | NH-s-C₄H₉ |
| —(CH₂)₂CH(CH₃)— | NHC₂H₅ |
| —(CH₂)₂CH(CH₃)— | NH-i-C₃H₇ |
| —(CH₂)₅— | NH-s-C₄H₉ |
| —(CH₂)₅— | NH-n-C₄H₉ |
| —(CH₂)₅— | N(CH₃)C₂H₅ |
| —(CH₂)₂CH(CH₃)CH₂— | NHCH₃ |
| —(CH₂)₂CH(CH₃)CH₂— | NH-n-C₄H₉ |
| —CH₂C(CH₃)₂CH₂— | NHCH₃ |
| —CH₂C(CH₃)₂CH₂— | NHC₂H₅ |
| —CH₂C(CH₃)₂CH₂— | N(CH₃)₂ |
| —CH₂C(CH₃)₂CH₂— | N(CH₃)C₂H₅ |
| —CH(CH₃)(CH₂)₃— | NHCH₃ |
| —CH(CH₃)(CH₂)₃— | NHC₂H₅ |
| —CH(CH₃)(CH₂)₃— | NH-i-C₃H₇ |
| —(CH₂)₂C(CH₃)₂— | N(CH₃)C₂H₅ |
| —C(CH₃)₂(CH₂)₂— | NHCH₃ |
| —C(CH₃)₂(CH₂)₂— | NHC₂H₅ |
| —C(CH₃)₂(CH₂)₂— | NH-n-C₃H₇ |

Preparation H

Haloalkyleneamines

The following haloalkyleneamine hydrohalides not previously reported in the chemical literature are synthesized by the procedure of Markova, et al., Zuhr. Obshchei Khim., 30, 1039 (1960) and comprises the reaction of a hydroxyalkyleneamine hydrochloride with an excess of thionyl chloride in an inert solvent at 50°–60° C. for 3–4 hours.

| NH₂—A—Cl.HCl | |
|---|---|
| A | A |
| —CH(CH₃)(CH₂)₂— | —CH₂C(CH₃)₂CH₂ |
| —CH(CH₃)CH(CH₃)— | —CH(CH₃)C(CH₃)₂— |
| —CH₂CH(C₂H₅)CH₂— | —CH(CH₃)(CH₂)₃— |
| —CH(C₃H₇)CH₂— | —C(CH₃)₂(CH₂)₂— |
| —CH(CH₃)CH₂CH(CH₃)— | |

Preparation I

The following β-ketoesters not previously reported in the chemical literature are synthesized by the procedure of Dorsch, et al., J. Am. Chem. Soc., 54, 2960 (1932) and comprises initial formation of a β-ketonitrile from acetonitrile and an appropriate ester, followed by alcoholysis of said nitrile with the requisite alcohol.

$$R_4-\overset{O}{\overset{\|}{C}}-CH_2-\overset{O}{\overset{\|}{C}}-O-A-Z$$

| $R_4$ | A | Z |
|---|---|---|
| $C_2H_5$ | $-(CH_2)_2-$ | $CH_3CO_2-$ |
| $C_2H_5$ | $-(CH_2)_4-$ | $CH_3CO_2-$ |
| $C_2H_5$ | $-(CH_2)_2-$ | $C_6H_5CO_2-$ |
| $C_2H_5$ | $-(CH_2)_2-$ | $4-BrC_6H_4CO_2-$ |
| $C_2H_5$ | $-(CH_2)_4-$ | $3-CH_3OC_6H_4CO_2-$ |
| $C_2H_5$ | $-CH_2C(CH_3)_2CH_2-$ | $CH_3CO_2-$ |
| $C_3H_7$ | $-(CH_2)_2-$ | $CH_3CO_2-$ |
| $C_3H_7$ | $-(CH_2)_2-$ | $CH_3CH_2CO_2-$ |
| $C_3H_7$ | $-(CH_2)_2CH(CH_3)-$ | $CH_3CO_2-$ |
| $C_3H_7$ | $-(CH_2)_5-$ | $CH_3CO_2-$ |
| $C_3H_7$ | $-CH(CH_3)CH_2CH(CH_3)-$ | $CH_3CO_2-$ |
| $C_3H_7$ | $-(CH_2)_2-$ | $4-ClC_6H_4CO_2-$ |
| $C_3H_7$ | $-(CH_2)_5-$ | $2-FC_6H_4CO_2-$ |
| $C_2H_5$ | $-(CH_2)_2-$ | $NHCH_3$ |
| $C_2H_5$ | $-(CH_2)_2-$ | $NHC_2H_5$ |
| $C_2H_5$ | $-(CH_2)_5-$ | $NHC_2H_5$ |
| $C_2H_5$ | $-(CH_2)_3-$ | $NHCH_3$ |
| $C_2H_5$ | $-(CH_2)_2-$ | $NHi-C_3H_7$ |
| $C_2H_5$ | $-(CH_2)_2CH(CH_3)-$ | $NHCH_3$ |
| $C_2H_5$ | $-(CH_2)_3-$ | $NHn-C_3H_7$ |
| $C_3H_7$ | $-(CH_2)_2-$ | $NHCH_3$ |
| $C_3H_7$ | $-(CH_2)_3-$ | $NHCH_3$ |
| $C_3H_7$ | $-(CH_2)_3-$ | $NHC_2H_5$ |
| $C_3H_7$ | $-(CH_2)_2-$ | $NHs-C_4H_9$ |
| $C_3H_7$ | $-(CH_2)_2-$ | $NHC_2H_5$ |
| $C_3H_7$ | $-CH(CH_3)CH_2-$ | $NHt-C_4H_9$ |
| $C_3H_7$ | $-(CH_2)_2-$ | $NHn-C_4H_9$ |
| $C_2H_5$ | $-(CH_2)_2-$ | $N(CH_3)_2$ |
| $C_2H_5$ | $-(CH_2)_2-$ | $N(CH_3)C_2H_5$ |
| $C_2H_5$ | $-(CH_2)_2-$ | $N(C_2H_5)_2$ |
| $C_2H_5$ | $-(CH_2)_3-$ | $N(CH_3)_2$ |
| $C_2H_5$ | $-(CH_2)_3-$ | $N(CH_3)C_2H_5$ |
| $C_2H_5$ | $-CH(CH_3)CH_2-$ | $N(CH_3)_2$ |
| $C_2H_5$ | $-CH_2CH(CH_3)-$ | $N(C_2H_5)_2$ |
| $C_2H_5$ | $-(CH_2)_2CH(CH_3)-$ | $N(CH_3)C_2H_5$ |
| $C_2H_5$ | $-(CH_2)_4-$ | $N(CH_3)_2$ |
| $C_2H_5$ | $-CH_2C(CH_3)_2CH_2-$ | $N(CH_3)C_2H_5$ |
| $C_2H_5$ | $-(CH_2)_4-$ | $N(C_2H_5)_2$ |
| $C_2H_5$ | $-(CH_2)_5-$ | $N(CH_3)_2$ |
| $C_3H_7$ | $-(CH_2)_2-$ | $N(CH_3)_2$ |
| $C_3H_7$ | $-(CH_2)_3-$ | $N(CH_3)_2$ |
| $C_3H_7$ | $-(CH_2)_3-$ | $N(CH_3)C_2H_5$ |
| $C_3H_7$ | $-CH_2CH(CH_3)-$ | $N(CH_3)C_2H_5$ |
| $C_3H_7$ | $-(CH_2)_4-$ | $N(C_2H_5)_2$ |
| $C_3H_7$ | $-(CH_2)_5-$ | $N(CH_3)_2$ |
| $C_3H_7$ | $-(CH_2)_5-$ | $N(C_2H_5)_2$ |

Preparation J

2-Acetonyl-1,3-oxazoline

To a solution of 8.5 g. (0.1 mole) of 2-methyl-1,3-oxazoline in 85 ml. of dry tetrahydrofuran, and cooled in an acetone-dry ice bath to −60° C., is added 6.4 g. (0.1 mole) of n-butyl lithium and the reaction mixture allowed to stir for 1 hour. To the cloudy solution is then added 7.8 g. (0.1 mole) of acetyl chloride at such a rate that the temperature is maintained below −50° C. The reaction mixture is allowed to warm to room temperature and is then filtered and the solvent removed in vacuo. The desired product is purified by distillation under reduced pressure.

Employing the above procedure and starting with the appropriate 2-methyl-1,3-oxazacyclic compound and either acetyl, propionyl, butyryl or iso-butyryl chloride the following compounds are thus prepared:

$$R_4-\overset{O}{\overset{\|}{C}}-CH_2-\overset{N-A}{\underset{O}{\diagdown\diagup}}$$

| $R_4$ | A | $R_4$ | A |
|---|---|---|---|
| $CH_3$ | $-(CH_2)_2-$ | $C_3H_7$ | $-(CH_2)_3-$ |
| $CH_3$ | $-(CH_2)_3-$ | $C_3H_7$ | $-CH_2CH(CH_3)-$ |
| $CH_3$ | $-CH(CH_3)CH_2-$ | $C_3H_7$ | $-(CH_2)_4-$ |
| $CH_3$ | $-CH_2CH(CH_3)-$ | $C_3H_7$ | $-(CH_2)_2-$ |
| $CH_3$ | $-(CH_2)_4-$ | | |
| $CH_3$ | $-CH_2CH(C_2H_5)CH_2-$ | | |
| $CH_3$ | $-(CH_2)_5-$ | | |
| $C_2H_5$ | $-(CH_2)_2-$ | | |
| $C_2H_5$ | $-(CH_2)_3-$ | | |
| $C_2H_5$ | $-(CH_2)_3CH(CH_3)-$ | | |

Preparation K

2-(2-Oxazolin-2-yl)-3-methylquinoxaline 1,4-dioxide

To a solution of 12.7 g. (0.1 mole) of 2-methyl-1,3-oxazoline in 100 ml. of ethanol containing 2.3 g. (0.03 mole) of sodium ethoxide is added 8.4 g. (0.1 mole) of benzofuroxan. The resulting mixture is heated to 50° C. for 3–4 hours and is then concentrated under reduced pressure to one-half its original volume and cooled. The resulting precipitate is suction filtered and recrystallized from methanol-chloroform. The product is identical to that prepared in Preparation B.

Starting with the appropriate benzofuroxan and 2-alkanoylmethyl-1,3-oxazacyclic compound the following analogs of the formula are thus prepared:

| X | $R_4$ | A |
|---|---|---|
| H | $CH_3$ | $-(CH_2)_2-$ |
| H | $CH_3$ | $-(CH_2)_3-$ |
| H | $CH_3$ | $-CH_2CH(CH_3)-$ |
| H | $C_2H_5$ | $-(CH_2)_2-$ |
| H | $C_2H_5$ | $-(CH_2)_3-$ |
| H | $C_3H_7$ | $-(CH_2)_2-$ |
| $CH_3$ | $CH_3$ | $-(CH_2)_4-$ |
| $CH_3$ | $CH_3$ | $-(CH_2)_5-$ |
| $CH_3$ | $C_2H_5$ | $-(CH_2)_2-$ |
| $CH_3$ | $C_3H_7$ | $-(CH_2)_2-$ |
| $OCH_3$ | $CH_3$ | $-(CH_2)_2-$ |
| $OCH_3$ | $CH_3$ | $-CH_2CH(C_2H_5)CH_2-$ |
| $OCH_3$ | $C_2H_5$ | $-(CH_2)_3-$ |
| $OCH_3$ | $C_3H_7$ | $-(CH_2)_3CH(CH_3)-$ |
| $CF_3$ | $CH_3$ | $-(CH_2)_2-$ |
| $CF_3$ | $CH_3$ | $-(CH_2)_3-$ |
| $CF_3$ | $C_2H_5$ | $-(CH_2)_2-$ |
| $CF_3$ | $C_2H_5$ | $-(CH_2)_3-$ |
| F | $CH_3$ | $-(CH_2)_4-$ |
| F | $CH_3$ | $-CH_2CH(C_2H_5)CH_2-$ |
| F | $C_3H_7$ | $-(CH_2)_2-$ |
| Cl | $CH_3$ | $-(CH_2)_2-$ |
| Cl | $C_2H_5$ | $-(CH_2)_3-$ |
| Cl | $C_2H_5$ | $-(CH_2)_3CH(CH_3)-$ |
| Br | $C_2H_5$ | $-(CH_2)_5-$ |
| Br | $C_3H_7$ | $-(CH_2)_3-$ |

What is claimed is:
1. 3-Methyl-2-quinoxalinecarboxylic acid, 2-aminoethyl ester, 1,4-dioxide.

* * * * *